(12) United States Patent
Aravamudan et al.

(10) Patent No.: US 12,259,864 B1
(45) Date of Patent: Mar. 25, 2025

(54) APPARATUS AND METHOD FOR TRAINING A MACHINE LEARNING MODEL

(71) Applicant: nference, Inc., Cambridge, MA (US)

(72) Inventors: Murali Aravamudan, Andover, MA (US); Ajit Rajasekharan, West Windsor, NJ (US)

(73) Assignee: nference, Inc., Cambridge, MA (US)

( * ) Notice: Subject to any disclaimer, the term of this patent is extended or adjusted under 35 U.S.C. 154(b) by 0 days.

(21) Appl. No.: 18/795,107

(22) Filed: Aug. 5, 2024

(51) Int. Cl.
*G06F 16/22* (2019.01)
*G06F 16/25* (2019.01)
*G16H 10/60* (2018.01)

(52) U.S. Cl.
CPC ............ *G06F 16/22* (2019.01); *G06F 16/256* (2019.01); *G16H 10/60* (2018.01)

(58) Field of Classification Search
CPC ........ G06F 16/22; G06F 16/256; G16H 10/60
See application file for complete search history.

(56) References Cited

U.S. PATENT DOCUMENTS

| | | | |
|---|---|---|---|
| 10,978,189 | B2 | 4/2021 | White et al. |
| 2017/0270250 | A1 | 9/2017 | Dettman et al. |
| 2019/0129593 | A1* | 5/2019 | Chein ............... G06Q 30/0239 |
| 2022/0270146 | A1* | 8/2022 | Diedrich ............. H04L 9/3236 |
| 2024/0127087 | A1* | 4/2024 | Goyal ..................... G06N 5/04 |

FOREIGN PATENT DOCUMENTS

| | | |
|---|---|---|
| CN | 116628171 A | 10/2023 |
| KR | 20220156363 A | 11/2022 |

OTHER PUBLICATIONS

E. Steinberg et al; Language Models Are An Effective Representation Learning Technique For Electronic Health Record Data; J Biomed Inform. Jan. 2021; 113: 103637.

\* cited by examiner

*Primary Examiner* — Cam Y T Truong
(74) *Attorney, Agent, or Firm* — Caldwell Intellectual Property Law

(57) ABSTRACT

Described herein is an apparatus and method for training a machine learning model. An apparatus may include a computing device configured to receive a corpus of data containing entries corresponding to a plurality of subjects; identify a plurality of entries within the corpus, corresponding to a first subject of the plurality of subjects and representing medical history of the first subject; determine a plurality of temporal attributes of the plurality of entries; generate a plurality of tokens as a function of the plurality of entries; generate a chronological data structure segment ordering one or more of the plurality of entries and the plurality of tokens, as a function of the plurality of temporal attributes; and train a multimodal machine learning model on a training dataset including the chronological data structure segment.

18 Claims, 12 Drawing Sheets

| | First Medical Event for First Subject | Second Medical Event for First Subject | ... |
|---|---|---|---|
| First Subject | First Medical Event for First Subject | Second Medical Event for First Subject | ... |
| Second Subject | First Medical Event for Second Subject | Second Medical Event for Second Subject | ... |
| Third Subject | First Medical Event for Third Subject | Second Medical Event for Third Subject | ... |
| | | | |

FIG. 2

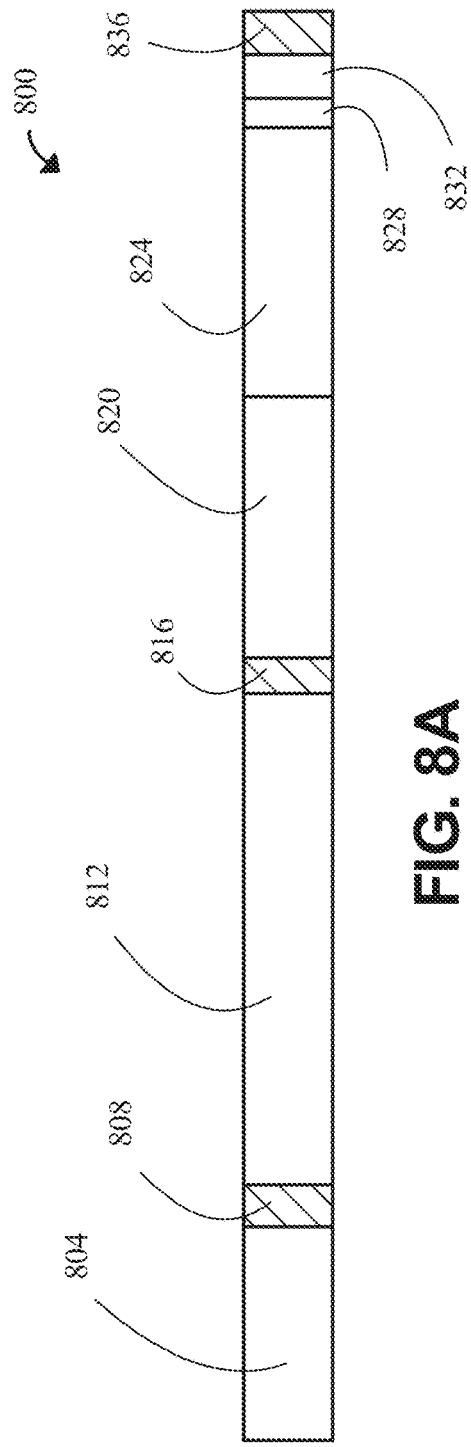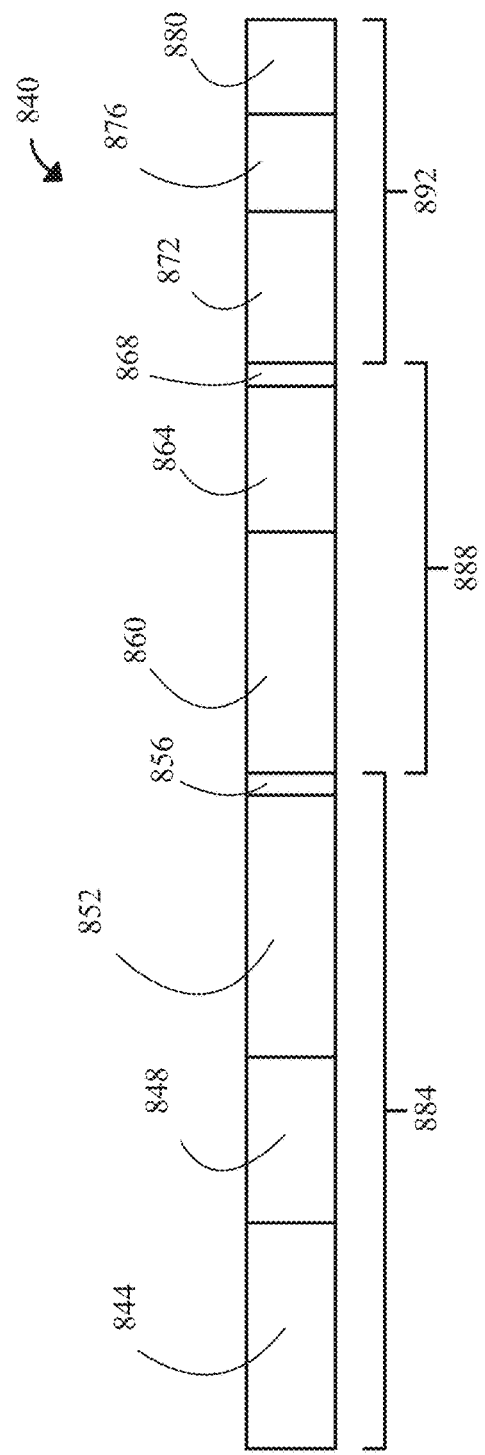

APPARATUS AND METHOD FOR TRAINING A MACHINE LEARNING MODEL

FIELD OF THE INVENTION

The present invention generally relates to the field of machine learning. In particular, the present invention is directed to an apparatus and method for training a machine learning model.

BACKGROUND

Many sets of data relating to specific events, such as digitized patient history, resides in dismembered or fragmented state across relational or non-relational data stores. In digitized storage, the organization of data may be driven by optimal storage and retrieval objectives, where relational database tables may be created to store timestamped information particular events. For example, where such events are medical tests, each table may store a specific test along with the doctor's notes for that test, for all patients undergoing that test.

SUMMARY OF THE DISCLOSURE

In an aspect, an apparatus for training a machine learning model may include at least a processor; and a memory communicatively connected to the at least processor, wherein the memory contains instructions configuring the at least processor to receive a corpus of data containing entries corresponding to a plurality of subjects; identify a plurality of entries within the corpus, corresponding to a first subject of the plurality of subjects and representing medical history of the first subject; determine a plurality of temporal attributes of the plurality of entries, wherein at least a temporal attribute of the plurality of temporal attributes is a temporal attribute of an entry of the plurality of entries, wherein a temporal attribute of the plurality of temporal attributes represents time within the medical history; generate a plurality of tokens as a function of the plurality of entries, wherein the plurality of tokens comprises tokens of a plurality of modalities; generate a chronological data structure segment ordering one or more of the plurality of entries and the plurality of tokens, as a function of the plurality of temporal attributes; and train a multimodal machine learning model on a training dataset including the chronological data structure segment.

In another aspect, a method for training a machine learning model may include, using at least a processor, receiving a corpus of data containing entries corresponding to a plurality of subjects; using the at least a processor, identifying a plurality of entries within the corpus, corresponding to a first subject of the plurality of subjects and representing medical history of the first subject; using the at least a processor, determining a plurality of temporal attributes of the plurality of entries, wherein at least a temporal attribute of the plurality of temporal attributes is a temporal attribute of an entry of the plurality of entries, wherein a temporal attribute of the plurality of temporal attributes represents time within the medical history; using the at least a processor, generating a plurality of tokens as a function of the plurality of entries, wherein the plurality of tokens comprises tokens of a plurality of modalities; using the at least a processor, generating a chronological data structure segment ordering one or more of the plurality of entries and the plurality of tokens, as a function of the plurality of temporal attributes; and using the at least a processor, training a multimodal machine learning model on a training dataset including the chronological data structure segment.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2 is a diagram depicting an exemplary embodiment of a chronological data structure;

FIG. 8A is a diagram depicting an exemplary embodiment of a chronological data structure;

FIG. 8B is a diagram depicting an exemplary embodiment of a chronological data structure;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a system, apparatus and method for training a machine learning model. In some embodiments, data of a particular subject may be stored in one or more databases and aggregated with data of other subjects. For example, subject medical data of a particular medical test may be stored in a medical database along with data of the same test type for other subjects. As described further herein, an apparatus may assemble such information into a training dataset including chronologically ordered data for a plurality of subjects. A system may train a machine learning model, such as a model with a long context length, based on such a dataset.

Figure 1:
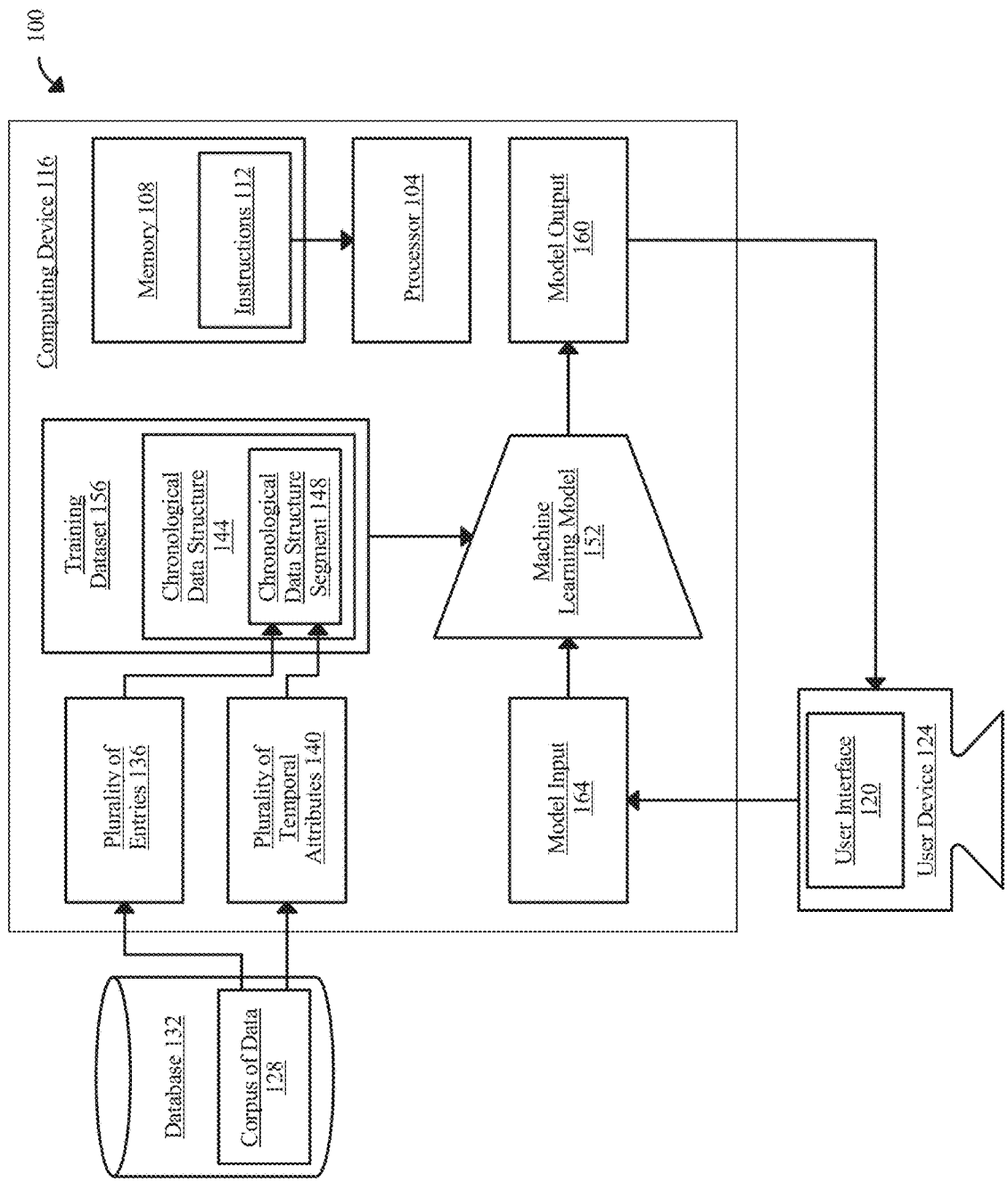
FIG. 1 is a diagram depicting an exemplary embodiment of an apparatus for training a machine learning model.

Referring now to FIG. 1, an exemplary embodiment of an apparatus 100 for training a machine learning model is illustrated. Apparatus 100 may include a computing device.

Apparatus 100 may include a processor. Processor may include, without limitation, any processor described in this disclosure. Processor may be included in computing device. Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device.

Still referring to FIG. 1, in some embodiments, apparatus 100 may include at least a processor 104 and a memory 108 communicatively connected to the at least a processor 104, the memory 108 containing instructions 112 configuring the at least a processor 104 to perform one or more processes described herein. Computing device 116 may include processor 104 and/or memory 108. Computing device 116 may be configured to perform one or more processes described herein.

Still referring to FIG. 1, computing device 116 may include but is not limited to, for example, a computing device or cluster of computing devices in a first location and a second computing device or cluster of computing devices in a second location. Computing device 116 may include one or more computing devices dedicated to data storage, security, distribution of traffic for load balancing, and the like. Computing device 116 may distribute one or more computing tasks as described below across a plurality of computing devices of computing device, which may operate in parallel, in series, redundantly, or in any other manner used for distribution of tasks or memory between computing devices. Computing device 116 may be implemented, as a non-limiting example, using a "shared nothing" architecture.

Still referring to FIG. 1, computing device 116 may be designed and/or configured to perform any method, method step, or sequence of method steps in any embodiment described in this disclosure, in any order and with any degree of repetition. For instance, computing device 116 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 116 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, as used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, in some embodiments, apparatus 100 includes user interface 120. User interface 120 may be a component of user device 124. User device 124 may include, in non-limiting examples, a smartphone, smartwatch, laptop computer, desktop computer, virtual reality device, or tablet. User interface 120 may include an input interface and/or an output interface. An input interface may include one or more mechanisms for a computing device to receive data from a user such as, in non-limiting examples, a mouse, keyboard, button, scroll wheel, camera, microphone, switch, lever, touchscreen, trackpad, joystick, and controller. An output interface may include one or more mechanisms for a computing device to output data to a user such as, in non-limiting examples, a screen, speaker, and haptic feedback system. An output interface may be used to display one or more elements of data described herein. As used herein, a device "displays" a datum if the device outputs the datum in a format suitable for communication to a user. For example, a device may display a datum by outputting text or an image on a screen or outputting a sound using a speaker.

Still referring to FIG. 1, in some embodiments, apparatus 100 receives corpus of data 128 corresponding to a plurality of subjects. In some embodiments, corpus of data 128 may include subject medical data obtained from one or more medical databases. As used herein, a "subject medical datum" is a datum describing the health of a subject, the medical history of a subject, or both. Subject medical data may include, in non-limiting examples, one or more data points indicating a height of a subject over time, a current weight of a subject, magnetic resonance imaging (MRI) data of a subject, electrocardiogram data of a subject, a diagnosis of a subject, a list of medications a subject was on at a particular date, and a record of a vaccination received by a subject. In some embodiments, one or more elements of subject medical data may include natural language. In a non-limiting example, subject medical data may include notes of a doctor on a checkup with a subject. Corpus of data 128 may include data of a variety of categories. Additional non-limiting examples of categories of data which corpus of data 128 may include are vehicle maintenance data and property sale data. In some embodiments, corpus of data 128 may be received from one or more databases 132. In some embodiments, corpus of data 128 may include data corresponding to a plurality of subjects or other objects for which there are multiple instances of data over time. As non-limiting examples, corpus of data 128 may include multiple instances of subject medical data of the same subject, multiple instances of vehicle maintenance data of the same vehicle, or multiple instances of property sale data of the same property. In some embodiments, corpus of data 128 is organized within database 132 and/or received from database 132 in a manner other than chronologically ordered and separated by subject. In a non-limiting example, subject medical data may be organized chronologically, but with all medical tests of a particular type and/or by a particular medical facility stored in the same data structure. In some embodiments, corpus of data 128 may be received from a plurality of databases. In a non-limiting example, subject medical data of a particular subject may be split across several medical databases, and computing device 116 may receive data from each such database in order to assemble corpus of data 128 including complete data as to that subject.

Still referring to FIG. 1, in some embodiments, corpus of data 128 may include image data. In a non-limiting example, subject medical data may include an image of handwritten doctor notes on a particular subject. In some embodiments, image data may be processed using optical character recognition. In some embodiments, optical character recognition or optical character reader (OCR) includes automatic conversion of images of written (e.g., typed, handwritten or printed text) into machine-encoded text. In some cases, recognition of at least a keyword from image data may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine-learning processes. In some cases, intelligent word recognition (IWR) may recognize written text, one word at a time, for instance by employing machine-learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information may make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image data. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image data to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image data. In some cases, binarization may be required for example if an employed OCR algorithm only works on binary images. In some cases, a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image data.

Still referring to FIG. 1, in some embodiments an OCR process may include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of image data. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into at least a feature. Exemplary non-limiting features may include corners, edges, lines, closed loops, line direction, line intersections, and the like. In some cases, feature extraction may reduce dimensionality of representation and may make the recognition process computationally more efficient. In some cases, extracted feature may be compared with an abstract vector-like representation of a character, which might reduce to one or more glyph prototypes. General techniques of feature detection in computer vision are applicable to this type of OCR. In some embodiments, machine-learning processes like nearest neighbor classifiers (e.g., k-nearest neighbors algorithm) may be used to compare image features with stored glyph features and choose a nearest match. OCR may employ any machine-learning process described in this disclosure, for example machine-learning processes described with reference to FIGS. 5-7. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. A first pass may try to recognize a character. Each character that is satisfactory is passed to an adaptive classifier as training data. The adaptive classifier then gets a chance to recognize characters more accurately as it further analyzes image data. Since the adaptive classifier may have learned something useful a little too late to recognize characters on the first pass, a second pass is run over the image data. Second pass may include adaptive recognition and use characters recognized with high confidence on the first pass to recognize better remaining characters on the second pass. In some cases, two-pass approach may be advantageous for unusual fonts or low-quality image data. Another exemplary OCR software tool include OCRopus. OCRopus development is led by German Research Centre for Artificial Intelligence in Kaiserslautern, Germany. In some cases, OCR software may employ neural networks.

Still referring to FIG. 1, in some cases, OCR may include post-processing. For example, OCR accuracy may be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of image data. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

Still referring to FIG. 1, in some embodiments, corpus of data 128 may include audio data. In non-limiting examples, subject medical data may include audio of a doctor speaking notes on a particular subject or notes on how a medical procedure went. audio data may be processed using automatic speech recognition. In some embodiments, automatic speech recognition may require training (i.e., enrollment). In some cases, training an automatic speech recognition model may require an individual speaker to read text or isolated vocabulary. In some cases, audio training data may include an audio component having an audible verbal content, the contents of which are known a priori by a computing device. Computing device may then train an automatic speech recognition model according to training data which includes audible verbal content correlated to known content. In this way, computing device may analyze a person's specific voice and train an automatic speech recognition model to the person's speech, resulting in increased accuracy. Alternatively, or additionally, in some cases, computing device may include an automatic speech recognition model that is speaker independent. As used in this disclosure, a "speaker independent" automatic speech recognition process is an automatic speech recognition process that does not require training for each individual speaker. Conversely, as used in this disclosure, automatic speech recognition processes that employ individual speaker specific training are "speaker dependent".

Still referring to FIG. 1, in some embodiments, an automatic speech recognition process may perform voice recognition or speaker identification. As used in this disclosure, "voice recognition" is a process of identifying a speaker, from audio content, rather than what the speaker is saying. In some cases, computing device may first recognize a speaker of verbal audio content and then automatically recognize speech of the speaker, for example by way of a speaker dependent automatic speech recognition model or process. In some embodiments, an automatic speech recognition process can be used to authenticate or verify an identity of a speaker. In some cases, a speaker may or may not include subject. For example, subject may speak within audio data, but others may speak as well.

Still referring to FIG. 1, in some embodiments, an automatic speech recognition process may include one or all of acoustic modeling, language modeling, and statistically based speech recognition algorithms. In some cases, an automatic speech recognition process may employ hidden Markov models (HMMs). As discussed in greater detail below, language modeling such as that employed in natural language processing applications like document classification or statistical machine translation, may also be employed by an automatic speech recognition process.

Still referring to FIG. 1, an exemplary algorithm employed in automatic speech recognition may include or even be based upon hidden Markov models. Hidden Markov models (HMMs) may include statistical models that output a sequence of symbols or quantities. HMMs can be used in speech recognition because a speech signal can be viewed as a piecewise stationary signal or a short-time stationary signal. For example, over a short time scale (e.g., 10 milliseconds), speech can be approximated as a stationary process. Speech (i.e., audible verbal content) can be understood as a Markov model for many stochastic purposes.

Still referring to FIG. 1, in some embodiments HMMs can be trained automatically and may be relatively simple and computationally feasible to use. In an exemplary automatic speech recognition process, a hidden Markov model may output a sequence of n-dimensional real-valued vectors (with n being a small integer, such as 10), at a rate of about one vector every 10 milliseconds. Vectors may consist of cepstral coefficients. A cepstral coefficient requires using a spectral domain. Cepstral coefficients may be obtained by taking a Fourier transform of a short time window of speech yielding a spectrum, decorrelating the spectrum using a cosine transform, and taking first (i.e., most significant) coefficients. In some cases, an HMM may have in each state a statistical distribution that is a mixture of diagonal covariance Gaussians, yielding a likelihood for each observed vector. In some cases, each word, or phoneme, may have a different output distribution; an HMM for a sequence of words or phonemes may be made by concatenating an HMMs for separate words and phonemes.

Still referring to FIG. 1, in some embodiments, an automatic speech recognition process may use various combinations of a number of techniques in order to improve results. In some cases, a large-vocabulary automatic speech recognition process may include context dependency for phonemes. For example, in some cases, phonemes with different left and right context may have different realizations as HMM states. In some cases, an automatic speech recognition process may use cepstral normalization to normalize for different speakers and recording conditions. In some cases, an automatic speech recognition process may use vocal tract length normalization (VTLN) for male-female normalization and maximum likelihood linear regression (MLLR) for more general speaker adaptation. In some cases, an automatic speech recognition process may determine so-called delta and delta-delta coefficients to capture speech dynamics and might use heteroscedastic linear discriminant analysis (HLDA). In some cases, an automatic speech recognition process may use splicing and a linear discriminate analysis (LDA)-based projection, which may include heteroscedastic linear discriminant analysis or a global semi-tied covariance transform (also known as maximum likelihood linear transform [MLLT]). In some cases, an automatic speech recognition process may use discriminative training techniques, which may dispense with a purely statistical approach to HMM parameter estimation and instead optimize some classification-related measure of training data; examples may include maximum mutual information (MMI), minimum classification error (MCE), and minimum phone error (MPE).

Still referring to FIG. 1, in some embodiments, an automatic speech recognition process may be said to decode speech (i.e., audible verbal content). Decoding of speech may occur when an automatic speech recognition system is presented with a new utterance and must compute a most likely sentence. In some cases, speech decoding may include a Viterbi algorithm. A Viterbi algorithm may include a dynamic programming algorithm for obtaining a maximum a posteriori probability estimate of a most likely sequence of hidden states (i.e., Viterbi path) that results in a sequence of observed events. Viterbi algorithms may be employed in context of Markov information sources and hidden Markov models. A Viterbi algorithm may be used to find a best path, for example using a dynamically created combination hidden Markov model, having both acoustic and language model information, using a statically created combination hidden Markov model (e.g., finite state transducer [FST] approach).

Still referring to FIG. 1, in some embodiments, speech (i.e., audible verbal content) decoding may include considering a set of good candidates and not only a best candidate, when presented with a new utterance. In some cases, a better scoring function (i.e., re-scoring) may be used to rate each of a set of good candidates, allowing selection of a best candidate according to this refined score. In some cases, a set of candidates can be kept either as a list (i.e., N-best list approach) or as a subset of models (i.e., a lattice). In some cases, re-scoring may be performed by optimizing Bayes risk (or an approximation thereof). In some cases, re-scoring may include optimizing for sentence (including keywords) that minimizes an expectancy of a given loss function with regards to all possible transcriptions. For example, re-scoring may allow selection of a sentence that minimizes an average distance to other possible sentences weighted by their estimated probability. In some cases, an employed loss function may include Levenshtein distance, although different distance calculations may be performed, for instance for specific tasks. In some cases, a set of candidates may be pruned to maintain tractability.

Still referring to FIG. 1, in some embodiments, an automatic speech recognition process may employ dynamic time warping (DTW)-based approaches. Dynamic time warping may include algorithms for measuring similarity between two sequences, which may vary in time or speed. For instance, similarities in walking patterns would be detected, even if in one video the person was walking slowly and if in another he or she were walking more quickly, or even if there were accelerations and deceleration during the course of one observation. DTW has been applied to video, audio, and graphics-indeed, any data that can be turned into a linear representation can be analyzed with DTW. In some cases, DTW may be used by an automatic speech recognition process to cope with different speaking (i.e., audible verbal content) speeds. In some cases, DTW may allow computing device to find an optimal match between two given sequences (e.g., time series) with certain restrictions. That is, in some cases, sequences can be "warped" non-linearly to match each other. In some cases, a DTW-based sequence alignment method may be used in context of hidden Markov models.

Still referring to FIG. 1, in some embodiments, an automatic speech recognition process may include a neural network. Neural network may include any neural network, for example those disclosed with reference to FIGS. 5-7. In some cases, neural networks may be used for automatic speech recognition, including phoneme classification, phoneme classification through multi-objective evolutionary algorithms, isolated word recognition, audiovisual speech recognition, audiovisual speaker recognition and speaker adaptation. In some cases, neural networks employed in automatic speech recognition may make fewer explicit assumptions about feature statistical properties than HMMs and therefore may have several qualities making them attractive recognition models for speech recognition. When used to estimate the probabilities of a speech feature segment, neural networks may allow discriminative training in a natural and efficient manner. In some cases, neural networks may be used to effectively classify audible verbal content over short-time interval, for instance such as individual phonemes and isolated words. In some embodiments, a neural network may be employed by automatic speech recognition processes for pre-processing, feature transformation and/or dimensionality reduction, for example prior to HMM-based recognition. In some embodiments, long short-term memory (LSTM) and related recurrent neural networks (RNNs) and Time Delay Neural Networks (TDNN's) may be used for automatic speech recognition, for example over longer time intervals for continuous speech recognition.

Still referring to FIG. 1, in some embodiments, computing device 116 may identify plurality of entries 136 within corpus of data 128 corresponding to a first subject of the plurality of subjects. Such plurality of subjects may include subjects whose data is described within corpus of data 128. In a non-limiting example, computing device 116 may identify subject medical data associated with a particular subject by extracting data entries with an identifier, such as a name or number, associated with a particular subject. In some embodiments, determining which entries contain a particular identifier may involve use of a process for conversion of data into a consistent format, such as use of optical character recognition. In additional non-limiting examples, where corpus of data 128 contains data describing vehicle maintenance history or property sales, computing device 116 may identify entries according to a number identifying a particular vehicle or a particular property. As described above, in some embodiments, such entries may represent a medical history of a subject.

Still referring to FIG. 1, in some embodiments, computing device 116 may determine plurality of temporal attributes 140. In some embodiments, each temporal attribute of plurality of temporal attributes 140 may be a temporal attribute of an entry of plurality of entries 136. In some embodiments, at least a temporal attribute of plurality of temporal attributes 140 may be a temporal attribute of an entry of plurality of entries 136. As used herein, a "temporal attribute" of an element of data is a point in time associated with the element of data, a range of time associated with the element of data, or both. In a non-limiting example, an entry may describe a trip by a subject to an emergency room, and an associated temporal attribute may include the date "Jun. 2, 2014." In another non-limiting example, an entry may describe a medical checkup of a subject, and an associated temporal attribute may include the time range "May 10, 2021, 3-3:30 pm." In some embodiments, identification of a temporal attribute may include retrieval of information from particular fields of data structures and/or digitized documents which typically contain temporal information, such as a field for a date. In some embodiments, identification of data in a form typically used to indicate a date, such as "Mar. 5, 2018" written in the top corner of handwritten doctors' notes. In some embodiments, a temporal attribute may represent time within a medical history of a subject.

Still referring to FIG. 1, in some embodiments, a temporal attribute machine learning model may be used to determine a temporal attribute. In some embodiments, a temporal attribute machine learning model may include a machine vision system trained using a machine learning process used to identify fields and/or sections of an image of corpus of data 128 likely to include a date. An optical character recognition system trained using a machine learning process may then be used to convert image data of such fields and/or sections into characters from which a temporal attribute such as a date may be determined. In another example, corpus of data 128 may include natural language including discussion of a particular date, and a temporal attribute machine learning model may include a language model used to determine whether such date is, as examples, a current date as of such discussion, or a date of another event. In another example, a temporal attribute machine learning model may include a language model used to determine the order of relevant events. In a non-limiting example, if a date of a medical procedure performed on a subject is known, and a language model interpretation of doctor's notes of a medical checkup indicate that the subject was discussing the results of the medical procedure, then a temporal attribute may be determined indicating that the medical checkup occurred after the medical procedure. In some embodiments, temporal attribute machine learning model may be trained using a supervised learning algorithm. Temporal attribute machine learning model may be trained on a training dataset including example entries, associated with example temporal attributes. Such a training dataset may be obtained by, for example, collecting entries and associated temporal attributes manually determined from those entries. Once temporal attribute machine learning model is trained, it may be used to determine one or more temporal attributes. Apparatus 100 may input an entry of plurality of entries 136 into temporal attribute machine learning model, and apparatus 100 may receive a temporal attribute from the model. In some embodiments, temporal attribute machine learning model may determine whether or not a temporal attribute may be determined from a particular entry.

Still referring to FIG. 1, in some embodiments, apparatus 100 may generate chronological data structure segment 144 comprising plurality of entries 136 using plurality of temporal attributes 140. As used herein, a "chronological data structure segment" is a data structure which includes chronologically ordered data associated with a single entity, a section of a data structure which includes chronologically ordered data associated with a single entity, or both. Data of a chronological data structure segment 144 may include, in non-limiting examples, subject medical data associated with a single subject, maintenance data associated with a single vehicle, or maintenance or sale data associated with a single property. Chronological data structure segment 144 may include, in non-limiting examples, a table, a row of a table, an array, and a linked list. Chronological data structure segment 144 may be a segment of chronological data structure 148. As used herein, a "chronological data structure" is a data structure which includes one or more chronological data structure segments. In some embodiments, a chronological data structure may include a dimension, such as a row of a table, which separates data of different entities, such as separation of subject medical data of different subjects. An exemplary chronological data structure is described below with reference to FIG. 2.

Still referring to FIG. 1, in some embodiments, chronological data structure 148 and/or chronological data structure segment 144 may be generated by assembling subject medical data from one or more medical databases. In some embodiments, computing device 116 may receive subject medical data, and determine the chronological order of such subject medical data, such as based on timestamps associated with subject medical data, and/or information within the subject medical data. In a non-limiting example, computing device 116 may determine a timestamp based on a date included in handwritten doctor's notes and processed using optical character recognition. Chronological data structure segment 144 may be generated by appending elements of subject medical data of a particular subject to chronological data structure segment 144 in order according to timestamps of such subject medical data. This may be repeated across multiple subjects to generate a dataset. In a non-limiting example, a chronological data structure segment may include subject medical data of a plurality of subjects divided into a plurality of chronological data structure segments of the chronological data structure. In some embodiments, each chronological data structure segment of a plurality of chronological data structure segments includes subject medical data of a single subject.

Still referring to FIG. 1, in some embodiments, receiving corpus of data 128 may include receiving entries from a plurality of databases 132 such as medical databases. In some embodiments, a chronological data structure segment may include an entirety of a subject's medical history which is recorded in such databases. As described below, in some embodiments, such lengthy chronological data structure segments may be used to train a machine learning model with long context lengths.

Still referring to FIG. 1, in some embodiments, apparatus 100 may train machine learning model 152 on training dataset 156 including chronological data structure segment 144. In some embodiments, machine learning model 152 may be trained using a supervised learning algorithm. For example, machine learning model 152 may be trained on a training dataset including chronologically earlier subject medical data, associated with medical outcomes found in chronologically later subject medical data. In another example, machine learning model 152 may be trained on a training dataset including subject medical data up to a certain time, associated with a medical diagnosis made at that time. Once machine learning model 152 is trained, it may be used to determine model output 160. Apparatus 100 may input a datum not part of training dataset 156, such as model input 164, into machine learning model 152, and apparatus 100 may receive model output 160 from the model. In some embodiments, model output 160 may include a medical prediction. As used herein, a "medical prediction" is a prediction, estimate, or both as to a medical state of a subject. In a non-limiting example, a machine learning model 152 input may include a medical history of a subject not in training dataset 156, and an output may include information as to a current health of the subject, such as information as to a medical condition the subject may have. Another non-limiting example of an output may include a prediction as to a future medical state of a subject, such as a medical condition the subject may develop in the future.

In some embodiments, machine learning model 152 may include a language model, such as a large language model (LLM). In some embodiments, a language model may be used to process subject medical data. As used herein, a "language model" is a program capable of interpreting natural language, generating natural language, or both. In some embodiments, a language model may be configured to interpret the output of an automatic speech recognition function and/or an OCR function. A language model may include a neural network. A language model may be trained using a dataset that includes natural language.

Still referring to FIG. 1, in some embodiments, a language model may be configured to extract one or more words from a document. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols. Textual data may be parsed into text tokens, which may include a simple word (sequence of letters separated by whitespace) or more generally a sequence of characters. As used herein, a "text token," is a smaller, individual grouping of text from a larger source of text. Text tokens may be broken up by word, pair of words, sentence, or other delimitations. Text tokens may in turn be parsed in various ways. Textual data may be parsed into words or sequences of words, which may be considered words as well. Textual data may be parsed into "n-grams", where all sequences of n consecutive characters are considered. Any or all possible sequences of text tokens or words may be stored as chains, for example for use as a Markov chain or Hidden Markov Model.

Still referring to FIG. 1, generating language model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, processor 104 may determine one or more language elements in subject medical data by identifying and/or detecting associations between one or more language elements (including phonemes or phonological elements, morphemes or morphological elements, syntax or syntactic elements, semantics or semantic elements, and pragmatic elements) extracted from at least subject medical data, including without limitation mathematical associations, between such words. Associations between language elements and relationships of such categories to other such term may include, without limitation, mathematical associations, including without limitation statistical correlations between any language element and any other language element and/or Language elements. Processor 104 may compare an input such as a sentence from subject medical data with a list of keywords or a dictionary to identify language elements. For example, processor 104 may identify whitespace and punctuation in a sentence and extract elements comprising a string of letters, numbers or characters occurring adjacent to the whitespace and punctuation. Processor 104 may then compare each of these with a list of keywords or a dictionary. Based on the determined keywords or meanings associated with each of the strings, processor 104 may determine an association between one or more of the extracted strings and a medical feature of a subject, a medical history of a subject, a medical procedure underwent by a subject, or the like, such as an association between a string containing the word "fracture" and a subject having broken a bone. Associations may take the form of statistical correlations and/or mathematical associations, which may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator May be determined, in an embodiment, by mathematical associations between detected words, comparisons to phrases and/or words indicating positive and/or negative indicators that are stored in memory.

Still referring to FIG. 1, processor 104 may be configured to determine one or more language elements in subject medical data using machine learning. For example, processor 104 may generate the language processing model by any suitable method, including without limitation a natural language processing classification algorithm; language processing model may include a natural language process classification model that enumerates and/or derives statistical relationships between input terms and output terms. An algorithm to generate language processing model may include a stochastic gradient descent algorithm, which may include a method that iteratively optimizes an objective function, such as an objective function representing a statistical estimation of relationships between terms, including relationships between input language elements and output patterns or conversational styles in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word, phrase, and/or other semantic unit. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Still referring to FIG. 1, processor 104 may be configured to determine one or more language elements in subject medical data using machine learning by first creating or receiving language classification training data. Training data may include data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name May be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, language classification training data may be a training data set containing associations between language element inputs and associated language element outputs. Language element inputs and outputs may be categorized by communication form such as written language elements, spoken language elements, typed language elements, or language elements communicated in any suitable manner. Language elements may be categorized by component type, such as phonemes or phonological elements, morphemes or morphological elements, syntax or syntactic elements, semantics or semantic elements, and pragmatic elements. Associations may be made between similar communication types of language elements (e.g. associating one written language element with another written language element) or different language elements (e.g. associating a spoken language element with a written representation of the same language element). Associations may be identified between similar communication types of two different language elements, for example written input consisting of the syntactic element "that" may be associated with written phonemes/th/, /ă/, and/t/. Associations may be identified between different communication forms of different language elements. For example, the spoken form of the syntactic element "that" and the associated written phonemes above. Language classification training data may be created using a classifier such as a language classifier. An exemplary classifier may be created, instantiated, and/or run using processor 104, or another computing device. Language classification training data may create associations between any type of language element in any format and other type of language element in any format. Additionally, or alternatively, language classification training data may associate language element input data to a feature related to a subject. For example, language classification training data may associate occurrences of the syntactic elements "irregular," and "heartbeat," in a single sentence with a potential cardiac disorder.

Still referring to FIG. 1, processor 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, processor 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

Still referring to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, language processing module may use a corpus of documents to generate associations between language elements in a language processing module, and a diagnostic engine may then use such associations to analyze words extracted from one or more documents and determine that the one or more documents indicate significance of a category. In an embodiment, a computing device may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into a computing device. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

Still referring to 1, machine learning model 152 may include a large language model (LLM). A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, entity documents, business documents, inventory documentation, emails, user communications, advertising documents, newspaper articles, and the like. In some embodiments, training sets of an LLM may include information from one or more public or private databases. As a non-limiting example, training sets may include databases associated with an entity. In some embodiments, training sets may include portions of documents associated with subject medical data correlated to examples of outputs. In an embodiment, an LLM may include one or more architectures based on capability requirements of an LLM. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM may be generally trained. As used in this disclosure, a "generally trained" LLM is an LLM that is trained on a general training set comprising a variety of subject matters, data sets, and fields. In some embodiments, an LLM may be initially generally trained. Additionally, or alternatively, an LLM may be specifically trained. As used in this disclosure, a "specifically trained" LLM is an LLM that is trained on a specific training set, wherein the specific training set includes data including specific correlations for the LLM to learn. As a non-limiting example, an LLM may be generally trained on a general training set, then specifically trained on a specific training set. In an embodiment, specific training of an LLM may be performed using a supervised machine learning process. In some embodiments, generally training an LLM may be performed using an unsupervised machine learning process. As a non-limiting example, specific training set may include information from a database. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in some embodiments an LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM may include a text prediction based algorithm configured to receive an article and apply a probability distribution to the words already typed in a sentence to work out the most likely word to come next in augmented articles. For example, if some words that have already been typed are "Nice to meet," then it may be highly likely that the word "you" will come next. An LLM may output such predictions by ranking words by likelihood or a prompt parameter. For the example given above, an LLM may score "you" as the most likely, "your" as the next most likely, "his" or "her" next, and the like. An LLM may include an encoder component and a decoder component.

Still referring to FIG. 1, an LLM may include a transformer architecture. In some embodiments, encoder component of an LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, an LLM and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM may predict the next word by searching for a set of positions in a source sentence where the most relevant information is concentrated. An LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, attention mechanism may include, without limitation, generalized attention self-attention, multi-head attention, additive attention, global attention, and the like. In generalized attention, when a sequence of words or an image is fed to an LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM may pick up particular parts at different positions in the input sequence and over time compute an initial composition of the output sequence. In multi-head attention, an LLM may include a transformer model of an attention mechanism. Attention mechanisms, as described above, may provide context for any position in the input sequence. For example, if the input data is a natural language sentence, the transformer does not have to process one word at a time. In multi-head attention, computations by an LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM may either attend to all source words or predict the target sentence, thereby attending to a smaller subset of words.

With continued reference to FIG. 1, multi-headed attention in encoder may apply a specific attention mechanism called self-attention. Self-attention allows models such as an LLM or components thereof to associate each word in the input, to other words. As a non-limiting example, an LLM may learn to associate the word "you" with "how" and "are." It's also possible that an LLM learns that words structured in this pattern are typically a question and to respond appropriately. In some embodiments, to achieve self-attention, input may be fed into three distinct fully connected neural network layers to create query, key, and value vectors. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referencing FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Continuing to refer to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens".

Still referring to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIG. 1, decoder may take this output and add it to the decoder inputs. Decoder may continue decoding until a token such as a text token is predicted. Decoder may stop decoding once it predicts an end token.

Continuing to refer to FIG. 1, in some embodiment, decoder may be stacked N layers high, with each layer taking in inputs from the encoder and layers before it. Stacking layers may allow an LLM to learn to extract and focus on different combinations of attention from its attention heads.

With continued reference to FIG. 1, an LLM may receive an input. Input may include a string of one or more characters. Inputs may additionally include unstructured data. For example, input may include one or more words, a sentence, a paragraph, a thought, a query, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like. In some embodiments, input may include any set of data associated with a subject medical datum.

With continued reference to FIG. 1, an LLM may generate at least one annotation as an output. At least one annotation may be any annotation as described herein. In some embodiments, an LLM may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

Still referring to FIG. 1, in some embodiments, machine learning model 152 may include a multimodal machine learning model. In some embodiments, machine learning model 152 may be trained on training dataset 156 including a plurality of entries including data of different modalities. In some embodiments, chronological data structure segment 144 may be generated based on a plurality of entries which include multimodal data. Chronological data structure segment 144 may include one or more tokens. As used herein, a "token" is an encoding of an element of data. Such an element of data may include data of plurality of entries 136. Tokens may describe and/or be associated with data of a variety of modalities. In non-limiting examples, tokens may describe text data, image data, and data describing the results of particular medical tests. For example, chronological data structure segment 144 may include a first token associated with doctor's notes in the form of text and a second token associated with an image, such as an image of an electrocardiogram readout or an image of a body part of a subject. Tokens associated with different modalities may be expressed using different token languages. For example, a first algorithm may be used to encode an image and a second algorithm may be used to encode text. In some embodiments, an embedding algorithm may be selected as a function of a file type of a file to be embedded. In some embodiments, chronological data structure segment 144 may include a plurality of chronologically ordered embeddings of data of plurality of entries 136. In some embodiments, a text sequence and a token specific to a non-text modality may be generated from the same element of subject medical data. In some embodiments, a token specific to a non-text modality may include a meta-token to be replaced and/or filled in using a modality specific encoder based on a segment of an entry such as a segment of subject medical data of a different modality than that used to generate a text sequence.

Still referring to FIG. 1, in some embodiments, training machine learning model 152, such as a large language model may include computing co-occurrences and/or joint probability distributions of tokens, such as tokens of different modalities. A machine learning model trained in this way may, for example, be capable of returning relevant information where an input includes an embedding of a first modality which indicates that a subject has a particular medical condition, and the training data includes embeddings of a second modality relevant to that condition.

Still referring to FIG. 1, in some embodiments, machine learning model 152 may include a neural network of at least a particular size and/or with at least a particular context length. In some embodiments, machine learning model 152 may have at least 1 billion, 10 billion, 100 billion, 1 trillion, or 10 trillion parameters. In some embodiments, machine learning model 152 may include a sufficient context length to include an entire patient medical history. Multimodal machine learning models are described further below with reference to FIG. 3.

Still-referring to FIG. 1, pseudo-code for an exemplary embodiment of an algorithm for chronological data structure 148 creation is provided below. In this example, data is presumed to be present in tabular form for simplicity of explaining the invention. The approach may apply to any form of storage, such as relational or non-relational storage mechanisms. Data present in storage may be text, multimodal data, and/or links to multimodal data. When non text data is flattened into a chronological data structure, modality specific encoders may be used to create tokens specific to that modality along with text. In some instances, a generated chronological data structure may have specialized meta tokens that trigger modality specific encoders to generate tokens or embeddings specific to that modality to fill in that position of a chronological data structure. While chronological data structure creation in the simplest case of text only corpus is a flattened sequence of text, in the multimodal corpus case, it may include a conceptually flattened sequence with interleaved placeholder directives to encode multimodal data, which may be invoked on the fly during training. Additionally, the proportion of each modality to train a specific model for optimal performance (e.g. image text, image, text ratio) can be decided leveraging the conceptually flattened corpus with embedded directives for each modality conversion to tokens/embeddings.

For patient_i in (list of all patients)
    Patient_history=[ ]
    For table_j in (list of all tables):
    Patient_history.append (patient record for patient_i in table_j)
    #end for
    Sort patient_history on timestamp
    Generate patient history treating each table column header as section header and the row content as the data under the section header.

Still referring to FIG. 1, in some embodiments, time stamp information may be provided by database 132 along with one or more entries. In some embodiments, such as where no explicit time stamp information is provided by database 132, apparatus 100 may infer and/or estimate time stamp information based on other information, as described above. In some embodiments, timestamp information need not be exact. For example, time stamp information may be deidentified and/or slightly altered but still maintain a sequence of events in order.

Still referring to FIG. 1, in some embodiments, one or more additional preprocessing steps may be applied to training dataset 156. For example, duplicates and/or spurious noise samples may be removed. In another example, data may be shuffled for batched model training, taking into account that a single subject history is a logical block.

Still referring to FIG. 1, in some embodiments, where patient history is generated for a row in a table, an LLM may be used to construct a "sentence form" of row contents, instead of only generating a section header and row content. This may be useful when, for example, flattening out a database table with multiple column measures. In some embodiments, where data from multiple tables is flattened, the tables themselves may be joined to create a composite view, which may be then flattened out as described by the pseudocode shown above.

Still referring to FIG. 1, in some embodiments, one or more aspects of apparatus 100 may be consistent with a feature disclosed in U.S. patent application Ser. No. 18/794,664, filed on Aug. 5, 2024, and titled "SYSTEMS AND METHODS FOR PREDICTION OF MEDICAL DISEASES", U.S. patent application Ser. No. 18/381,873, filed on Oct. 19, 2023, and titled "SYSTEMS AND METHODS FOR COMPUTING WITH PRIVATE HEALTHCARE DATA," and/or U.S. patent application Ser. No. 18/385,057, filed on Oct. 30, 2023, and titled "APPARATUS AND A METHOD FOR ANONYMIZING USER DATA," the entirety of each of which is hereby incorporated by reference. In a non-limiting example, a machine learning model described by U.S. patent application Ser. No. 18/794,664 may be trained using a training dataset assembled as described herein. In additional non-limiting examples, patient data may be de-identified as described in U.S. patent application Ser. No. 18/381,873 and/or U.S. patent application Ser. No. 18/385,057.

Still referring to FIG. 1, in some embodiments, apparatus 100 may deidentify one or more elements of data used to train machine learning model 152 and/or one or more elements of data to be input into machine learning model 152. For example, apparatus 100 may deidentify an element of subject medical data to be used in training dataset 156. In another example, apparatus 100 may deidentify model input 164. Deidentification of data such as subject medical data may include removal of a datum which may be used to identify a subject, such as, in non-limiting examples, a name of a subject, an address of a subject, and/or an account number associated with a subject. In some embodiments, deidentification of a subject medical datum may include alteration of a timestamp and/or temporal attribute associated with the subject medical datum. In some embodiments, such alteration of a timestamp and/or temporal attribute may be done while maintaining a temporal attribute's chronological order relative to other temporal attributes of entries associated with the same entity and/or subject.

Still referring to FIG. 1, in some embodiments, a chronological data structure segment may be split. This may be done, for example, where model sequence length is limited and cannot capture an entire set of data in a chronological data structure segment. In some embodiments, such splitting may be performed at a point between 2 chronologically adjacent entries. This may be done, for example, to preserve data of entries. In some embodiments, a split may be performed such that a temporal sequence of a history of an entity is honored on each side of the split. In a multimodal case, splitting may keep associated data, such as subject medical data, together when performing splitting. For example, an image and an associated caption may be kept together during a split. In some embodiments, one or more elements of data may be duplicated such that they are preserved on both sides of a split.

Still referring to FIG. 1, in some embodiments, machine learning model 152 may be trained using one or more supervised training steps after initial self-supervised learning. In some embodiments, supervised training of machine learning model 152 may include supervised fine tuning, which may, for example, teach the model to respond to questions with answers rather than responding to a question with another related question. In some embodiments, supervised training of machine learning model 152 may teach the model to generate responses that best answer a question, such as by scoring multiple answers to a question and using a loss function to modify the model based on its choice of the best answer to a question. This may be implemented using, for example, direct preference optimization and/or reinforced learning with human feedback.

Still referring to FIG. 1, in some embodiments, machine learning model 152 may be trained to produce a function call as an output. Such a function call may enable machine learning model 152 to perform external actions and/or generate outputs based on data generated using other methods. For example, if machine learning model 152 receives an input which it is not equipped to handle (for example, based on a level of confidence in the model's output and/or training data indicating that the model should perform a function call in response to certain categories of input), machine learning model 152 may perform a function call to a function specialized in handling and/or generating a response based on such input. For example, in the case of machine learning model 152 including a large language model, machine learning model 152 may call another program to perform arithmetic in order to produce a more reliable answer. In some embodiments, machine learning model 152 may use an outside program to generate a first component of an output and may itself produce a second component of an output. In a non-limiting example, machine learning model 152 including a language model may use an outside program to perform arithmetic and may itself generate language describing the context of the answer to the arithmetic problem. In some embodiments, machine learning model 152 may be trained to recognize inputs specifying the model's role in a conversation and/or in generating an output. For example, an input may indicate that a particular function is to be called in order to generate an output.

Still referring to FIG. 1, in some embodiments, machine learning model 152, once trained, may be run on a computing device in communication with one or more user devices. This may, for example, be used where machine learning model 152 includes a large number of parameters, making it memory and/or bandwidth inefficient for it to be stored on user devices. In some embodiments, machine learning model 152, once trained, may be run local to a user device. This may be used, for example, where machine learning model 152 is sufficiently small such that memory and/or bandwidth requirements for distribution of the model are low. In some embodiments, machine learning model 152 may be used to train a second machine learning model. Such second machine learning model may, for example, be trained on a training dataset including inputs and outputs of machine learning model 152. Such second machine learning model may, in some embodiments, be trained to handle a reduced scope of inputs and/or may include a model with fewer parameters. In some embodiments, distillation and/or other teacher student approaches may be used to train second machine learning model using machine learning model 152. In some embodiments, second machine learning model 152 may be minimally fine tuned for a particular area and/or type of input then distilled to create a smaller model. In some embodiments, inputs and/or outputs of machine learning model 152 may be used to train a plurality of additional machine learning models, such as a plurality of models specialized for particular tasks and/or types of input. In some embodiments, creation of a corpus for training/tuning an agent, such as creation of a corpus using machine learning model 152, is done as a function of the sequence length of machine learning model 152 and/or a model to be trained from such corpus so that a single sequence captures all information the model is to learn from.

Still referring to FIG. 1, in some embodiments, apparatus 100 may display a datum described herein, such as model output 160 to a user. Apparatus 100 may display a datum to a user using user interface 120. Apparatus 100 may generate a visual element and/or visual element data structure as a function of a datum described herein and display the visual element to a user. In some embodiments, a visual element data structure may include a visual element. As used herein, a "visual element" is a datum that is displayed visually to a user. In some embodiments, a visual element data structure may include a rule for displaying visual element. In some embodiments, a visual element data structure may be determined as a function of model output 160. In some embodiments, a visual element data structure may be determined as a function of an item from the list consisting of model input 164 and model output 160. In a non-limiting example, a visual element data structure may be generated such that visual element describing or highlighting model output 160 is displayed to a user. For example, a visual element may include a medical condition that a subject is predicted to have along with a description of such medical condition.

Still referring to FIG. 1, in some embodiments, visual element may include one or more elements of text, images, shapes, charts, particle effects, interactable features, and the like. For example, a visual element may include an interactable feature including a name of a medical condition a user is predicted to have, where hovering over the medical condition may cause display of a description of the medical condition.

Still referring to FIG. 1, a visual element data structure may include rules governing if or when visual element is displayed. In a non-limiting example, a visual element data structure may include a rule causing a visual element describing model output 160 to be displayed when a user selects model output 160 using a graphical user interface (GUI).

Still referring to FIG. 1, a visual element data structure may include rules for presenting more than one visual element, or more than one visual element at a time. In an embodiment, about 1, 2, 3, 4, 5, 10, 20, or 50 visual elements are displayed simultaneously.

Still referring to FIG. 1, a visual element data structure rule may apply to a single visual element or datum, or to more than one visual element or datum. For example, a visual element data structure may rank visual elements and/or other data and/or apply numerical values to them, and a computing device may display a visual element as a function of such rankings and/or numerical values. A visual element data structure may apply rules based on a comparison between such a ranking or numerical value and a threshold. For example, a visual element data structure may rank visual elements associated with medical conditions based on the severity of such condition.

Still referring to FIG. 1, in some embodiments, visual element may be interacted with. For example, visual element may include an interface, such as a button or menu. In some embodiments, visual element may be interacted with using a user device such as a smartphone.

Still referring to FIG. 1, in some embodiments, apparatus 100 may transmit visual element data structure to user device 124. In some embodiments, visual element data structure may configure user device 124 to display visual element. In some embodiments, visual element data structure may cause an event handler to be triggered in an application of user device 124 such as a web browser. In some embodiments, triggering of an event handler may cause a change in an application of user device 124 such as display of visual element.

Still referring to FIG. 1, in some embodiments, apparatus 100 may transmit visual element to a display. A display may communicate visual element to user. A display may include, for example, a smartphone screen, a computer screen, or a tablet screen. A display may be configured to provide a visual interface. A visual interface may include one or more virtual interactive elements such as, without limitation, buttons, menus, and the like. A display may include one or more physical interactive elements, such as buttons, a computer mouse, or a touchscreen, that allow user to input data into the display. Interactive elements may be configured to enable interaction between a user and a computing device. In some embodiments, a visual element data structure is determined as a function of data input by user into a display.

Still referring to FIG. 1, a variable and/or datum described herein may be represented as a data structure. In some embodiments, a data structure may include one or more functions and/or variables, as a class might in object-oriented programming. In some embodiments, a data structure may include data in the form of a Boolean, integer, float, string, date, and the like. In a non-limiting example, a subject medical datum data structure may include a string value representing doctor notes. In some embodiments, data in a data structure may be organized in a linked list, tree, array, matrix, tenser, and the like. In a non-limiting example, chronological data structure 148 may be organized in an array. In some embodiments, a data structure may include or be associated with one or more elements of metadata. A data structure may include one or more self-referencing data elements, which processor 104 may use in interpreting the data structure. In a non-limiting example, a data structure may include "<date>" and "</date>," tags, indicating that the content between the tags is a date.

Still referring to FIG. 1, a data structure may be stored in, for example, memory 108 or a database. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 1, in some embodiments, a data structure may be read and/or manipulated by processor 104. In a non-limiting example, a chronological data structure may be read and used to train machine learning model 152.

Still referring to FIG. 1, in some embodiments, a data structure may be calibrated. In some embodiments, a data structure may be trained using a machine learning algorithm. In a non-limiting example, a data structure may include an array of data representing the biases of connections of a neural network. In this example, the neural network may be trained on a set of training data, and a back propagation algorithm may be used to modify the data in the array. Machine learning models and neural networks are described further herein.

Referring now to FIG. 2, an exemplary embodiment of chronological data structure 200 is provided. Chronological data structure 200 may include, for a particular subject, one or more elements of subject medical data indicating one or more medical events, such as medical events 204 and 208. Such a medical event may include, in non-limiting examples, medical procedures, doctor appointments, and medical tests. In some embodiments, one or more medical events may be ordered chronologically and may be associated with a particular subject, such as subject 212. In some embodiments, data elements of chronological data structure 200 may be multimodal. For example, a first medical event may include text data representing doctor notes and a second medical event may include image data from an MRI. In some embodiments, chronological data structure 200 may include timestamp data associated with one or more medical events. Chronological data structure 200 may extend beyond dimensions depicted in FIG. 2, such as by including data of additional subjects and/or additional medical events for each subject.

Figure 3:
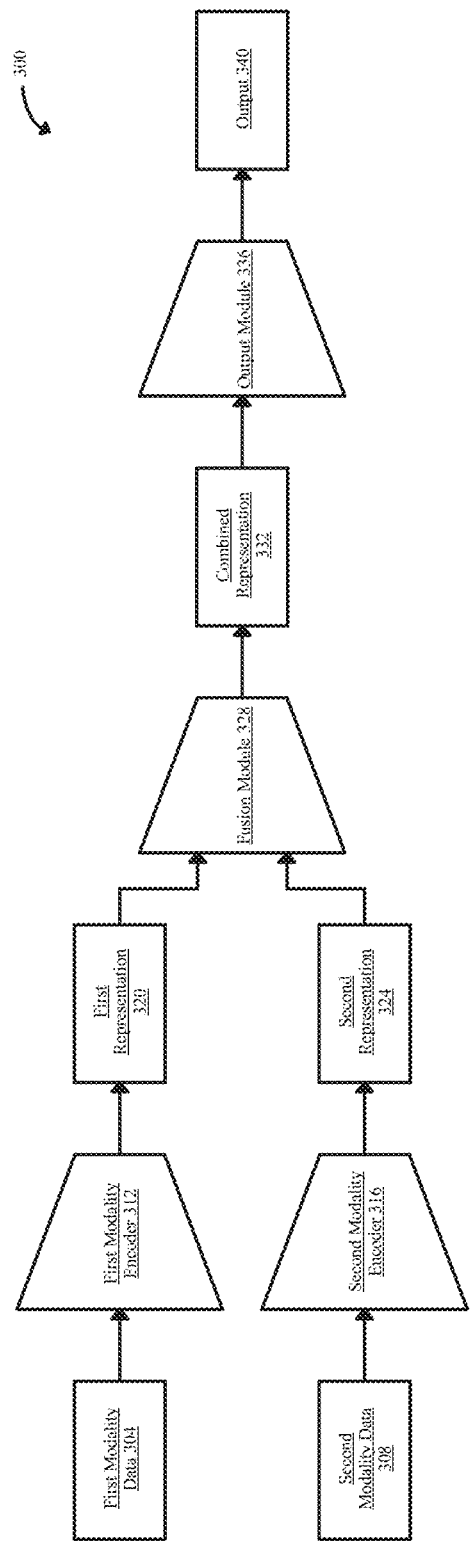
FIG. 3 is a block diagram of an exemplary embodiment of a multimodal neural network.

Referring now to FIG. 3, a block diagram of an exemplary embodiment of a multimodal neural network 300 is provided. As used herein, a "multimodal neural network" is a set of one or more neural networks which together accept inputs of a plurality of modes. In some embodiments, inputs of a plurality of modes may be used to generate a single output. Multimodal neural network 300 may include first modality data 304 and second modality data 308. First modality data 304 and/or second modality data 308 may include, in non-limiting examples, text data, electrocardiogram data, MRI data, and audio data. Such data may be of different modes. Non-limiting examples of differing modalities include image data, text data, and audio data. In some embodiments, a multimodal neural network may include a plurality of unimodal neural networks, such as first modality encoder 312 and second modality encoder 316. Each such unimodal neural network may accept an input of a single mode and may output an encoding of such input. Outputs of such unimodal neural networks may include mathematical representations of the input data. An encoder may be chosen according to the type of data to be encoded. First modality encoder 312 may output first representation 320 and second modality encoder 316 may output second representation 324. Fusion module 328 may be used to join information of a plurality of modalities. Fusion module 328 may include, in non-limiting examples, concatenation of first representation 320 and second representation 324, taking weighted sums of first representation 320 and second representation 324, application of a transformer network, and application of an attention based recurrent neural network. Fusion module 328 may output combined representation 332. In some embodiments, a cross-attention layer mechanism may be used to generate combined representation 332. In some embodiments, multimodal neural network 300 may accept as inputs data of more than 2 modalities, and multiple cross-attention mechanisms may be used. For example, if representations of data of a first, second, and third modality are used, then cross-attention mechanisms may be used to capture interactions between the first and second modalities, between the first and third modalities, between the second and third modalities, and between the first, second and third modalities. Combined representation 332 may be input into output module 336 in order to produce output 340. Output 340 may include, for example, a PFA durability datum. Output module 336 may include a machine learning model such as a neural network.

Still referring to FIG. 3, in some embodiments, a multimodal neural network may include an alignment module. An alignment module may cause generated representations to be similar across different input modalities. In some embodiments, a multimodal neural network may include a translation module. A translation module may be used to map data of a first modality to a second modality. In some embodiments, a multimodal neural network may be trained using co-learning. Co-learning may include transfer of information across modalities when training a model.

Still referring to FIG. 3, in some embodiments, a multimodal neural network may function by making a plurality of predictions based on data of a single modality and combining such predictions. For example, voting schemes or weighted averages may be used to determine a multimodal prediction from a plurality of unimodal predictions.

Figure 4:
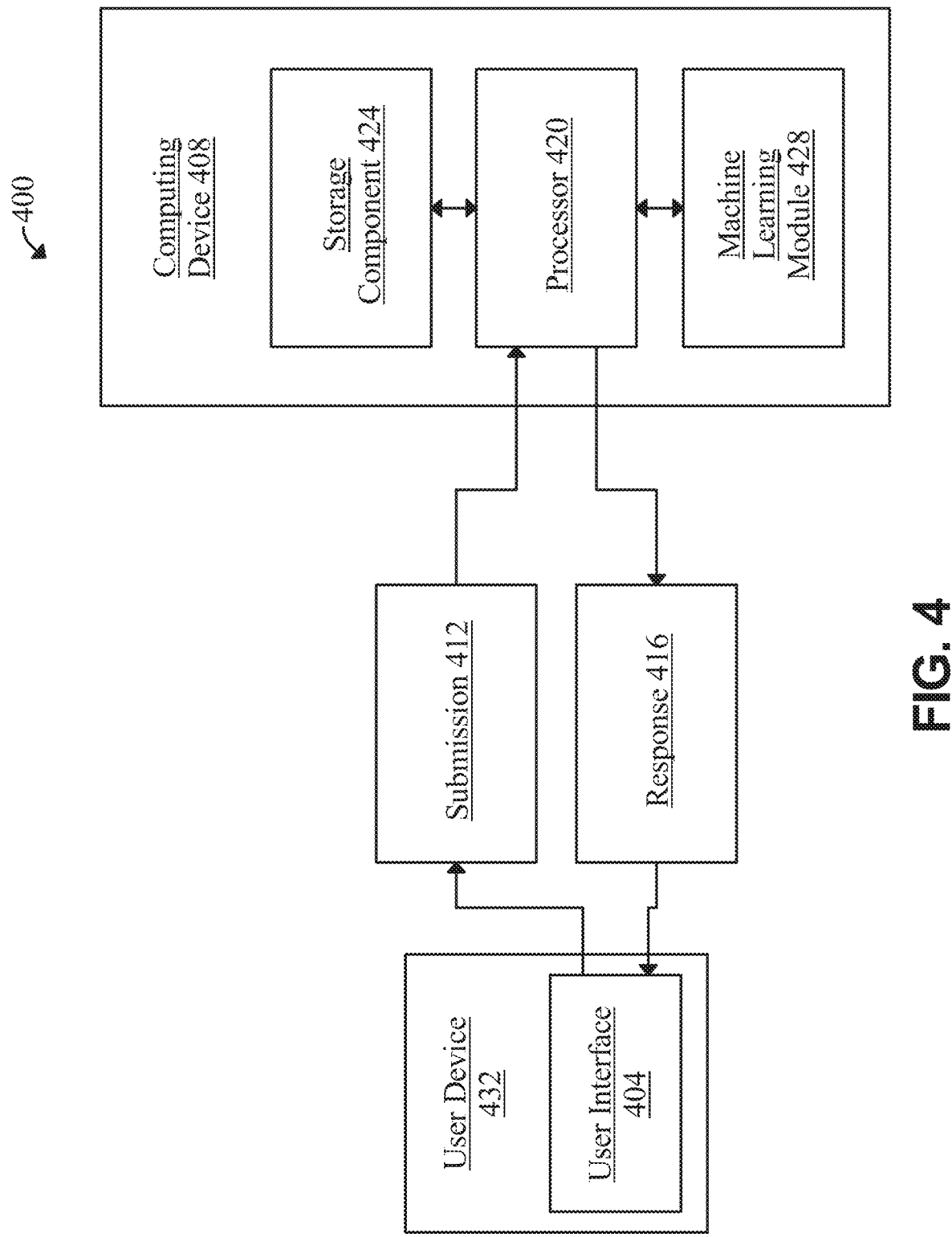
FIG. 4 is a block diagram of an exemplary apparatus including a chatbot.

Now referring to FIG. 4, in some embodiments, apparatus 400 may communicate with user and/or instructor using a chatbot. According to some embodiments, user interface 404 on user device 432 may be communicative with a computing device 408 that is configured to operate a chatbot. In some embodiments, user interface 404 may be local to user device 432. In some embodiments, user interface 404 may be local to computing device 408. Alternatively, or additionally, in some cases, user interface 404 may remote to user device 432 and communicative with user device 432, by way of one or more networks, such as without limitation the internet. Alternatively, or additionally, one or more user interfaces may communicate with computing device 408 using telephonic devices and networks, such as without limitation fax machines, short message service (SMS), or multimedia message service (MMS). Commonly, user communicate with computing device 408 using text-based communication, for example without limitation using a character encoding protocol, such as American Standard for Information Interchange (ASCII). Typically, user interfaces conversationally interface with a chatbot, by way of at least a submission, from a user interface to the chatbot, and a response, from the chatbot to the user interface. For example, user interface 404 may interface with a chatbot using submission 412 and response 416. In some embodiments, submission 412 and/or response 416 may use text-based communication. In some embodiments, submission 412 and/or response 416 may use audio communication.

Still referring to FIG. 4, submission 412, once received by computing device 408 operating a chatbot, may be processed by a processor 420. In some embodiments, processor 420 processes submission 412 using one or more of keyword recognition, pattern matching, and natural language processing. In some embodiments, processor employs real-time learning with evolutionary algorithms. In some cases, processor 420 may retrieve a pre-prepared response from at least a storage component 424, based upon submission 412. Alternatively or additionally, in some embodiments, processor 420 communicates a response 416 without first receiving a submission, thereby initiating conversation. In some cases, processor 420 communicates an inquiry to user interface 404; and processor 420 is configured to process an answer to the inquiry in a following submission from the user interface. In some cases, an answer to an inquiry present within a submission from a user device may be used by computing device 408 as an input to another function. In some embodiments, computing device 408 may include machine learning module 428. Machine learning module 428 may include any machine learning models described herein. In some embodiments, submission 412 may be input into a trained machine learning model within machine learning module 428. In some embodiments, submission 412 may undergo one or more processing steps before being input into a machine learning model. In some embodiments, submission 412 may be used to train a machine learning model within machine learning module 428.

Figure 5:
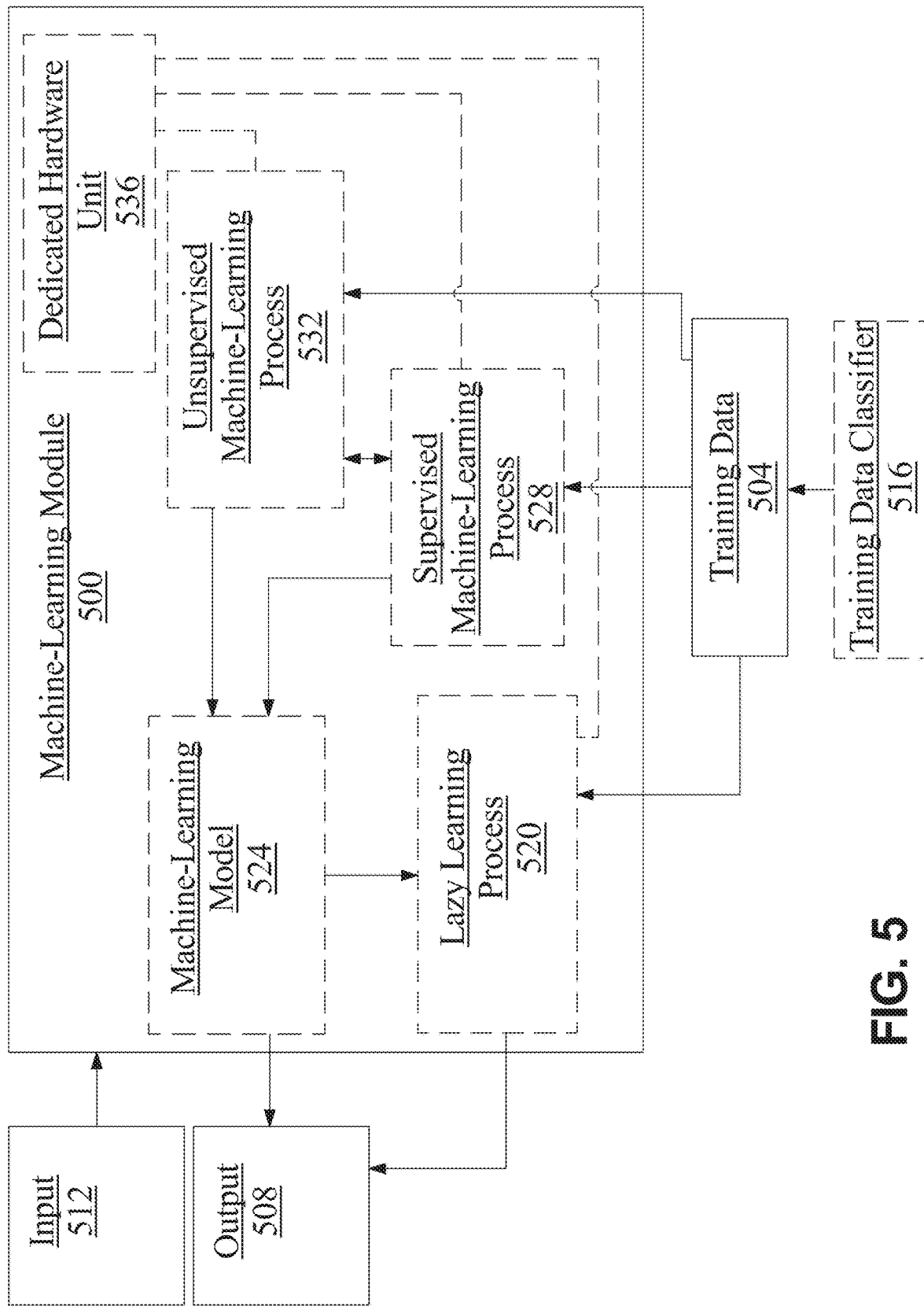
FIG. 5 is a block diagram of an exemplary embodiment of a machine learning model.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm instantiated in hardware or software logic, data structures, and/or functions that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example, inputs may include subject medical data and outputs may include medical predictions.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to particular modalities and/or populations.

Still referring to FIG. 5, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)=P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 5, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 5, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 5, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 5, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 5, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 5, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 5, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 5, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 5, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 5, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}:X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the 25th percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 5, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include subject medical data as described above as inputs, outputs as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

With further reference to FIG. 5, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 5, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 532 may not require a response variable; unsupervised processes 532 may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 5, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 5, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 5, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 5, one or more processes or algorithms described above may be performed by at least a dedicated hardware unit 536. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 536 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 536 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 536 to perform one or more operations described herein, such as evaluation of model and/or algorithm outputs, one-time or iterative updates to parameters, coefficients, weights, and/or biases, and/or any other operations such as vector and/or matrix operations as described in this disclosure.

With continued reference to FIG. 5, apparatus 100 may use user feedback to train the machine-learning models and/or classifiers described above. For example, classifier may be trained using past inputs and outputs of classifier. In some embodiments, if user feedback indicates that an output of classifier was "bad," then that output and the corresponding input may be removed from training data used to train classifier, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of classifier may include user feedback.

With continued reference to FIG. 5, in some embodiments, an accuracy score may be calculated for classifier using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons and used as described above. Accuracy score or another score as described above may indicate a degree of retraining needed for a machine-learning model such as a classifier; apparatus 100 may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

Figure 6:
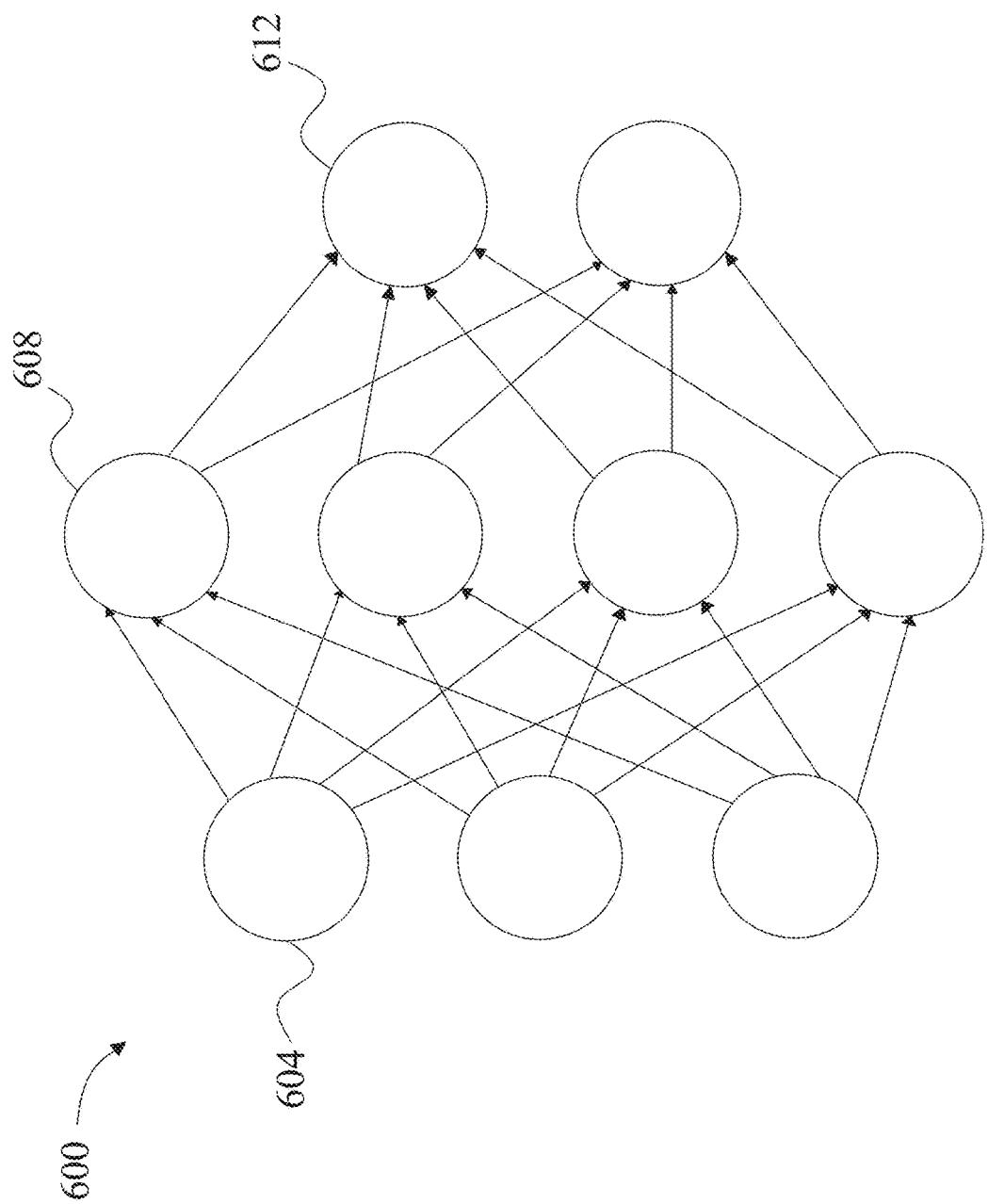
FIG. 6 is a schematic diagram of an exemplary embodiment of a neural network.

Referring now to FIG. 6, an exemplary embodiment of neural network 600 is illustrated. A neural network 600 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 604, one or more intermediate layers 608, and an output layer of nodes 612. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes.

Figure 7:
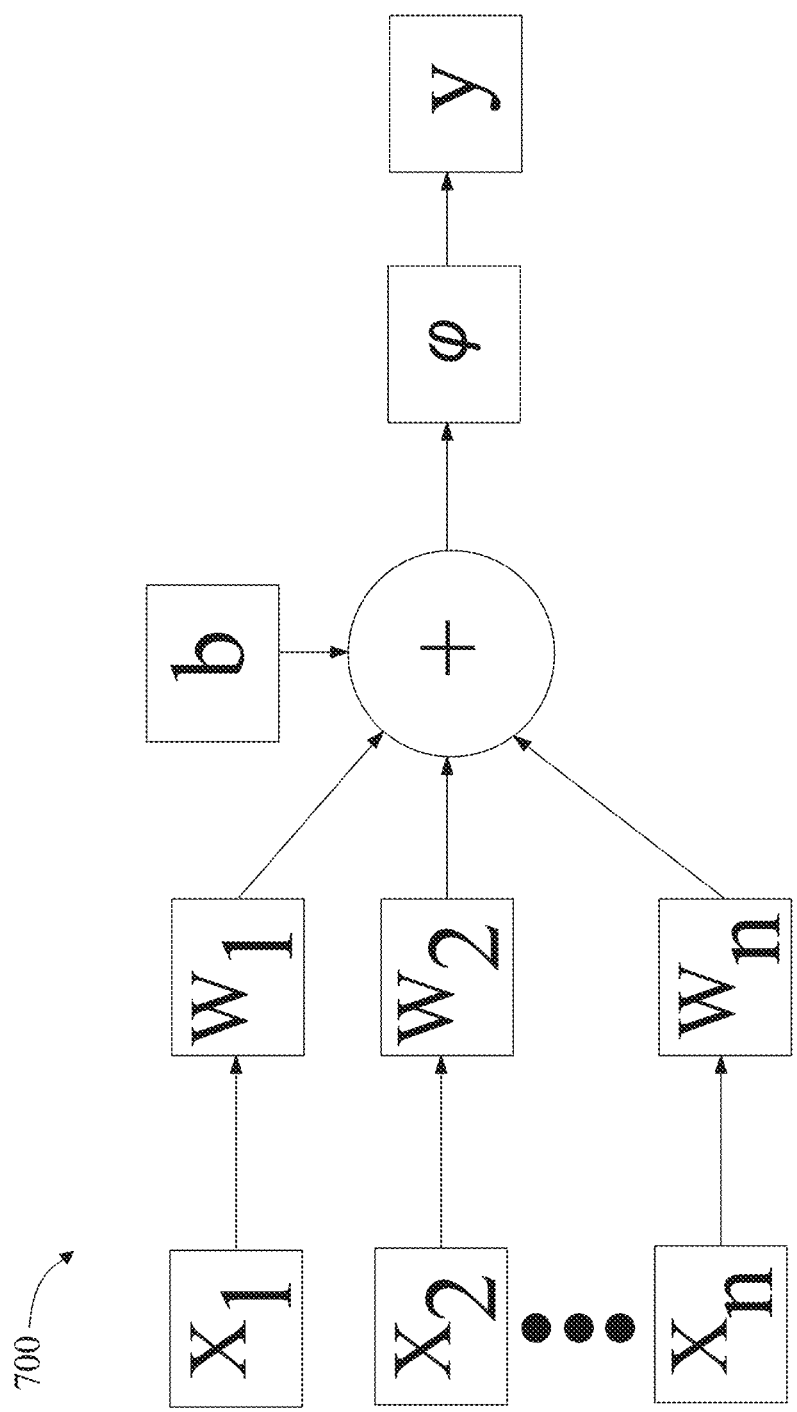
FIG. 7 is a schematic diagram of an exemplary embodiment of a neural network node.

Referring now to FIG. 7, an exemplary embodiment of a node 700 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^x}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+b^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs x; that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function q, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 7, a "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like. CNN may include, without limitation, a deep neural network (DNN) extension, where a DNN is defined as a neural network with two or more hidden layers.

Still referring to FIG. 7, in some embodiments, a convolutional neural network may learn from images. In non-limiting examples, a convolutional neural network may perform tasks such as classifying images, detecting objects depicted in an image, segmenting an image, and/or processing an image. In some embodiments, a convolutional neural network may operate such that each node in an input layer is only connected to a region of nodes in a hidden layer. In some embodiments, the regions in aggregate may create a feature map from an input layer to the hidden layer. In some embodiments, a convolutional neural network may include a layer in which the weights and biases for all nodes are the same. In some embodiments, this may allow a convolutional neural network to detect a feature, such as an edge, across different locations in an image.

Referring now to FIG. 8A, an exemplary embodiment of a chronological data structure is provided. In some embodiments, when encoding a plurality of entries and/or an entire patient history, temporally distinct sections may be explicitly separated. For example, a patient may come in year 2018 for an acute event and there is a whole bunch of diagnostic tests and subsequent interventions that happen in a short 3 day period necessitating an ICU admission etc; the patient is healthy for the next 6 years and comes in only for "occasional" checkups, say every 6 months or a year; then the patient has another acute episode in 2024 which necessitates another set of tests and interventions again in a short period. In some embodiments, the encoding scheme (the "flattening algorithm") may benefit from "explicit" separation in the stream. In some embodiments, such acute encoding periods may be performed distinctly again, such as in the same or another model. In some embodiments, such distinct streams may then be related. In some embodiments, a tight cluster of temporal events may be captured for co-occurrences—not mixing up 2018 events with 2024 events but at the same time, "as peeling of onion layers", capable of reasoning about the previous cluster as applicable. In some embodiments, temporally distinct sections of a plurality of entries and/or an entire patient history are not explicitly separated.

Still referring to FIG. 8A, in some embodiments, chronological data structure 800 may include one or more tokens such as tokens 804, 808, 812, 816, 820, 824, 828, 832 and/or 836. In some embodiments, one or more tokens of chronological data structure 800, such as tokens 804, 812, 820, 824, 828, and 832 may include one or more substantive tokens. As used herein, a "substantive token" is a token which represents data describing one or more elements of a medical history of a subject. Such elements may include, in non-limiting examples, doctor's notes, results of medical tests applied to a user, and records of medications taken by a user. In some embodiments, one or more tokens of chronological data structure 800, such as tokens 808, 816 and/or 836, may include one or more temporal tokens. As used herein, a "temporal token" is a token which represents a particular time. In some embodiments, a temporal token may represent a particular point in time. In some embodiments, a temporal token may represent a particular time range. In some embodiments, a temporal token may be tied to one or more substantive tokens, such as an adjacent substantive token. For example, a first temporal token may represent a time at which a preceding substantive token depicting an image of a subject was captured. In another example, a first temporal token may represent a time at which an associated substantive token depicting a doctor's note was recorded.

Referring now to FIG. 8B, in some embodiments, chronological data structure 840 may include one or more tokens such as tokens 844, 848, 852, 856, 860, 864, 868, 872, 876 and/or 880. In some embodiments, such tokens may be ordered chronologically. Such tokens may include substantive tokens and/or temporal tokens. In some embodiments, one or more sets of such tokens may represent a subject's medical history over a particular time range, such as a day, week, month, year, or decade. For example, chronological data structure 840 may include first time range 884, second time range 888, and third time range 892. In some embodiments, a chronological data structure segment may be created with an end at the end of a particular time range and/or with boundaries consistent with those of a particular time range. In some embodiments, a time range may end when there is a sufficiently large gap between consecutive elements of medical data of a subject.

Figure 9:
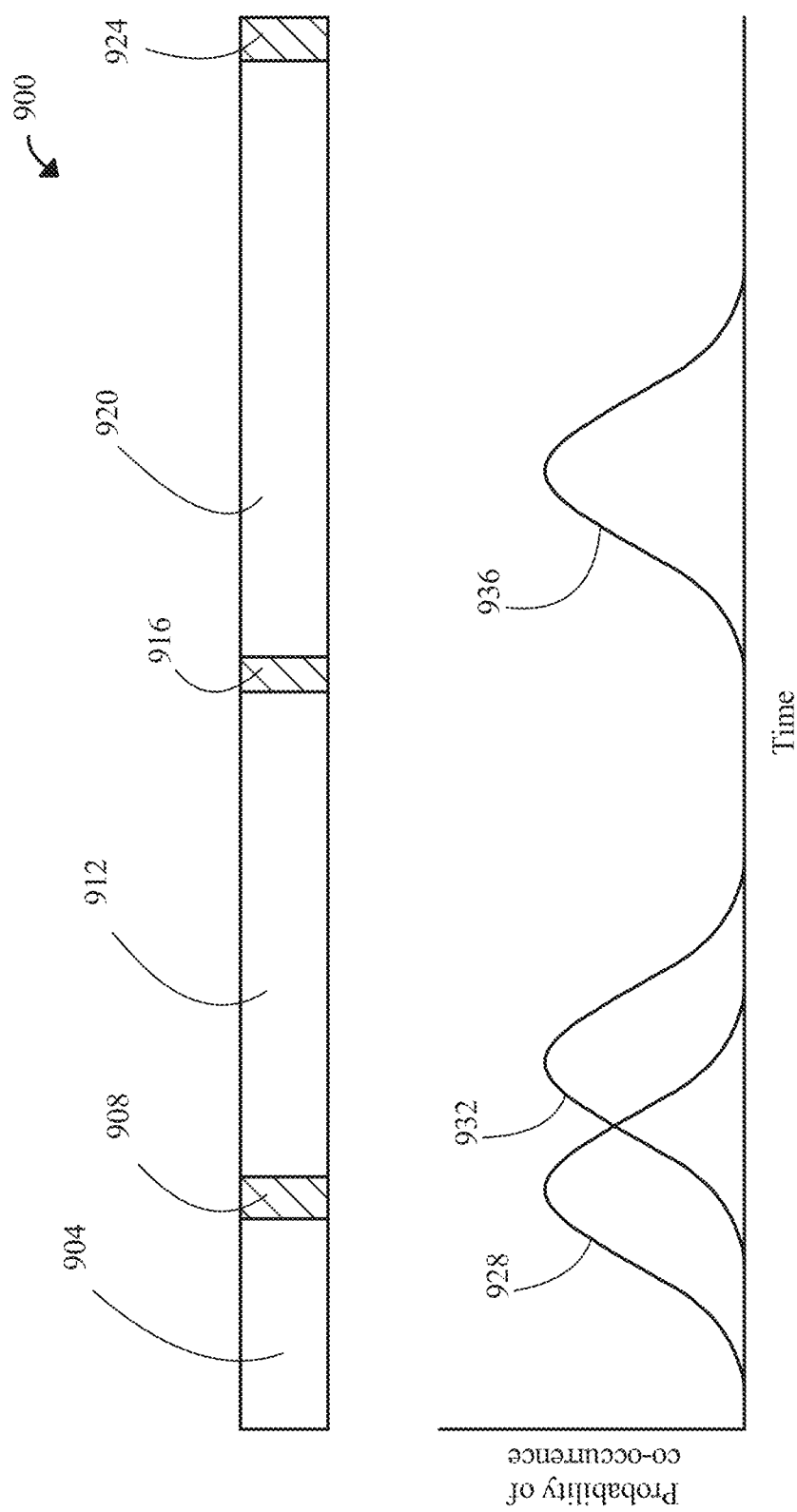
FIG. 9 is a diagram depicting an exemplary embodiment of a chronological data structure.

Referring now to FIG. 9, an exemplary embodiment of a chronological data structure is provided. One may "encode" temporal events as "tokens" in a "sequence", where every modality is expressed in terms of its own "token" language (be it, text, images etc.). In some embodiments, a Large Language Model may be able to compute "co-occurrences" and/or "Joint Probability Distributions of these tokens. This is especially powerful when the LLM is very large (such as 100s of billions or trillions of parameters) and the "context" size can easily encompass an "entire patient's history". In some embodiments, this innovation may be most relevant in the context of very large neural networks such as in multimodal neural networks such as GPT-4o, Claude Opus, or similar models.

Still referring to FIG. 9, in some embodiments, chronological data structure 900 may include one or more substantive tokens, such as tokens 904, 912, and 920. In some embodiments, chronological data structure 900 may include one or more temporal tokens, such as tokens 908, 916, and 924. In some embodiments, one or more temporal tokens may be associated with one or more substantive tokens. For example, token 904 may be associated with token 908. In some embodiments, a computing device may determine a probability of temporal co-occurrence of features represented by substantive tokens. For example, such probabilities may be determined based on one or more curves such as curves 928, 932, and/or 936. In some embodiments, a probability of co-occurrence may be determined as a function of the degree to which such curves overlap. In some embodiments, a curve may be associated with a substantive token and/or a temporal token. In some embodiments, a location of a curve may be determined based on a time point identified by a temporal token. In some embodiments, a shape of a curve, such as a standard deviation of a normal curve, may be determined based on an associated substantive token and/or temporal token. For example, a larger standard distribution may be used where a temporal token is less precise. In another example, a substantive token may indicate that a subject has a particular medical condition, and a curve shape may be determined based on the medical condition, such as by assigning larger standard deviations to normal curves associated with medical conditions which last longer.

Figure 10:
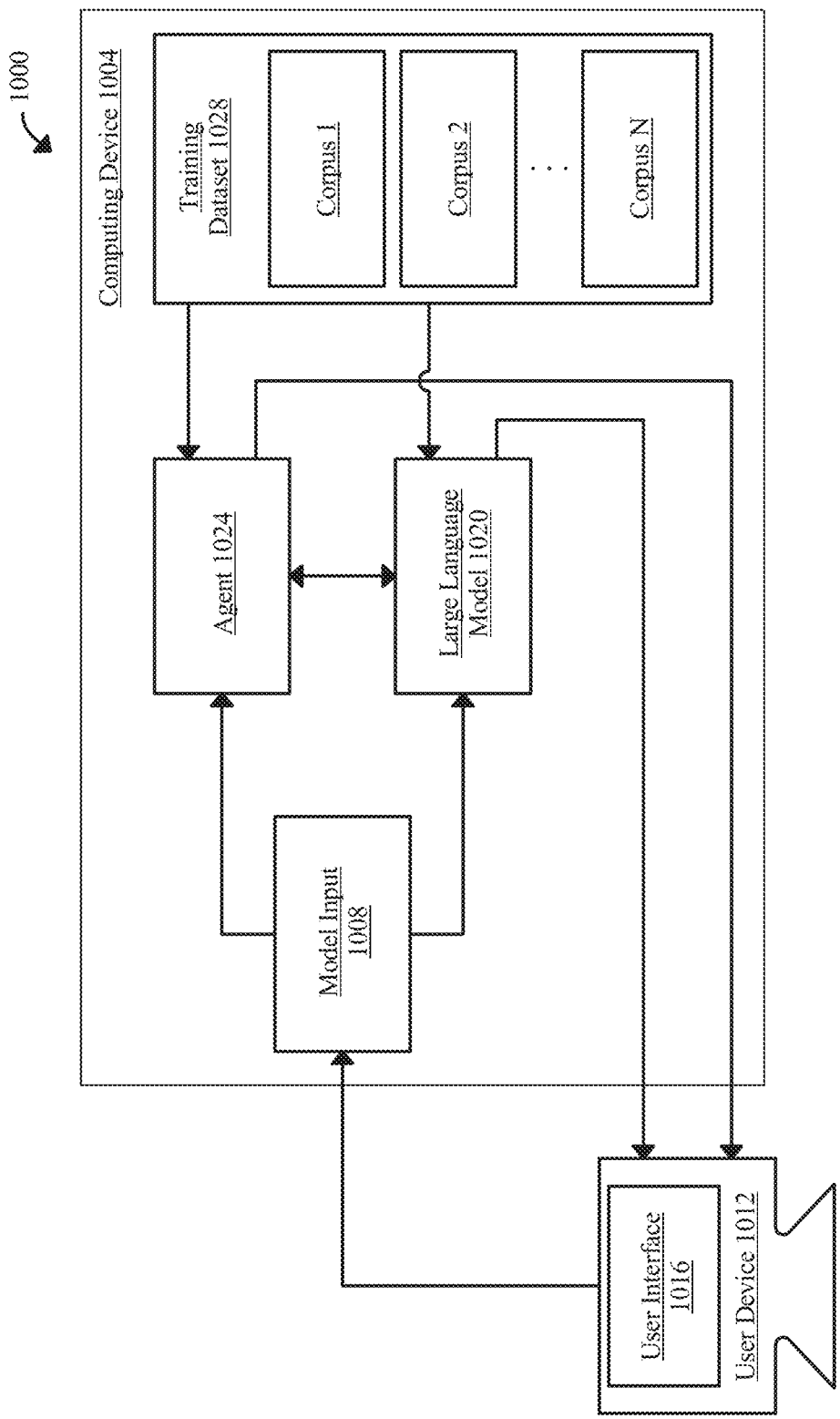
FIG. 10 is a diagram depicting an exemplary embodiment of an apparatus for training a machine learning model.

Referring now to FIG. 10, an exemplary embodiment of an apparatus 1000 for training a machine learning model is illustrated. In some embodiments, apparatus 1000 may be used for corpus creation for efficient training of agents. Large models may go through a series of subsequent supervised training steps after their initial self-supervised training on a corpus. These subsequent training steps, which are supervised, accomplish two things: First, they teach the model to respond to questions with answers and not just respond to question with another related question (this step is often called supervised fine tuning). Second, they teach the model to generate responses that best answers a question (this step often scores multiple answers to a question and the model is rewarded based on its choice of the best answer to a question-multiple approaches to do this—one of which is called DPO—direct preference optimization and the other older approach is RLHF—Reinforced learning with human feedback—although the latter is still claimed to be superior in some benchmarks).

Still referring to FIG. 10, the outcome of this training yields models like ChatGPT. Models may be trained to generate output resembling a function call (like in a programming language). This capability enables using the large models as agents to do external actions. For instance, LLMs are poor at arithmetic, but one can leverage a simple calculator function (written in some programming language) to be invoked by a model for the question "what is 12435+534543543?". Then equipped with such a function, a model may call the calculator function and return the answer as opposed to trying to compute it on its own. In general, an agent is a large model that, during inference time, knows to call the right functions to get a job done. An agent's task is often specified by a prompt that describes the agent's role in a conversation.

Still referring to FIG. 10, while one could argue a large model that is pretrained on a domain of interest could power an agent for that domain, there are use cases, where the model is best suited to be local to a device. Also, the scope of the task may be so narrow and specific, it might not require a large model with many parameters. While typical smaller models are created from large models by methods like distillation and more broadly teacher student approaches, there could be merit in minimally fine tuning a model for a specific area and then distilling it to create a smaller model. So, regardless of the approach, having a corpus tuned for a specific agent training has merit for reasons stated above. For this reason, an apparatus for corpus creation could create corpora (be it for pertaining or fine tuning) targeted for specific agents. Additionally, such agents could cooperate with other agents, some of which serve as broad experts while some other domain specific experts to solve tasks. The creation of the corpus for training/tuning an agent is done factoring the sequence length of the model so that a single sequence captures all the information we want the model to learn from.

Still referring to FIG. 10, in some embodiments, apparatus 1000 may include computing device 1004. Computing device 1004 may receive model input 1008 from user device 1012, which may include user interface 1016. Model input 1008 may be input into large language model 1020 and/or agent 1024. Large language model 1020 and/or agent 1024 may be trained using training dataset 1028. In some embodiments, inputs to and outputs from large language model 1020 may be used to train agent 1024. In some embodiments, agent 1024 does not include a machine learning model. For example, agent 1024 may include a computer program configured to perform a mathematical calculation or perform another task not suitable for a language model. In some embodiments, large language model 1020 may call agent 1024 and use a product of agent 1024 to generate an output. In some embodiments, an output of agent 1024 and/or large language model 1020 may be transmitted to user device 1012.

Still referring to FIG. 10, in some embodiments, a training step of a machine learning model such as agent 1024 and/or large language model 1020 may include determining co-occurrence of features of different modalities within training dataset 1028. For example, a training step may include determining whether a first token of a first modality has the same or similar meaning as a second token of a second modality. In some embodiments, tokens may be determined to have the same or similar meanings where they frequently co-occur in a set of training data. In a non-limiting example, a token representing text from a doctor's note saying a patient's collar bone is fractured may be determined to have the same or similar meaning as a token representing x-ray image data depicting fractured collar bones.

Figure 11:
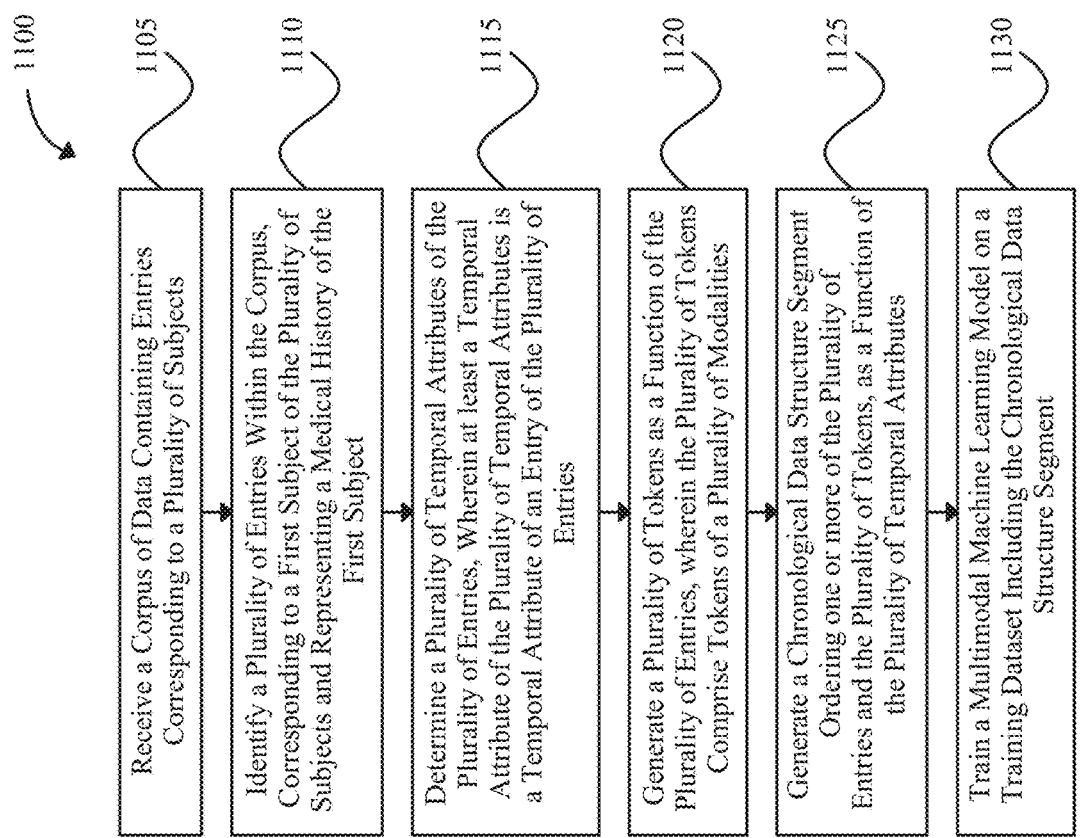
FIG. 11 is a flow diagram depicting an exemplary embodiment of a method of training a machine learning model.

Referring now to FIG. 11, an exemplary embodiment of a method 1100 of training a machine learning model is illustrated. One or more steps if method 1100 may be implemented, without limitation, as described with reference to other figures. One or more steps of method 1100 may be implemented, without limitation, using at least a processor.

Still referring to FIG. 11, in some embodiments, method 1100 may include a step 1105 of receiving a corpus of data containing entries corresponding to a plurality of subjects.

Still referring to FIG. 11, in some embodiments, method 1100 may include a step 1110 of identifying a plurality of entries within the corpus, corresponding to a first subject of the plurality of subjects and representing medical history of the first subject.

Still referring to FIG. 11, in some embodiments, method 1100 may include a step 1115 of determining a plurality of temporal attributes of the plurality of entries, wherein at least a temporal attribute of the plurality of temporal attributes is a temporal attribute of an entry of the plurality of entries. In some embodiments, determining the plurality of temporal attributes includes training a temporal attribute machine learning model on a training dataset including a plurality of example entries correlated to a plurality of example temporal attributes; and generating a temporal attribute as a function of a second entry using the trained temporal attribute machine learning model. In some embodiments, a temporal attribute of the plurality of temporal attributes may represent time within a medical history.

Still referring to FIG. 11, in some embodiments, method 1100 may include a step 1120 of generating a plurality of tokens as a function of the plurality of entries, wherein the plurality of tokens comprise tokens of a plurality of modalities.

Still referring to FIG. 11, in some embodiments, method 1100 may include a step 1125 of generating a chronological data structure segment ordering the one or more of the plurality of entries and the plurality of tokens as a function of the plurality of temporal attributes. In some embodiments, receiving the corpus of data comprises receiving entries from a plurality of medical databases; and the chronological data structure segment includes an entirety of the first subject's medical history which is recorded in the plurality of medical databases.

Still referring to FIG. 11, in some embodiments, method 1100 may include a step 1130 of training a multimodal machine learning model on a training dataset including the chronological data structure segment. In some embodiments, the machine learning model is a multimodal machine learning model; and the plurality of entries comprise data of different modalities. In some embodiments, generating the chronological data structure segment comprises generating both a text sequence and a modality specific token as a function of a first entry of the plurality of entries. In some embodiments, the training dataset comprises a chronological data structure comprising the chronological data structure segment; and the chronological data structure comprises subject medical data of a plurality of subjects divided into a plurality of chronological data structure segments of the chronological data structure. In some embodiments, the training dataset includes a chronological data structure comprising the chronological data structure segment; and the chronological data structure comprises entries of the plurality of entries which are associated with a plurality of subjects. In some embodiments, each chronological data structure segment of the plurality of chronological data structure segments comprises entries of a single subject. In some embodiments, training the multimodal machine learning model comprises computing co-occurrences of tokens of different modalities.

Still referring to FIG. 11, in some embodiments, method 1100 may further include deidentifying a third entry. In some embodiments, deidentifying the third entry comprises altering a temporal attribute associated with the third entry, while preserving the temporal attribute's chronological order relative to other temporal attributes of entries associated with the same subject. In some embodiments, method 1100 may further include splitting the chronological data structure segment at a point between two chronologically adjacent entries.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 12:
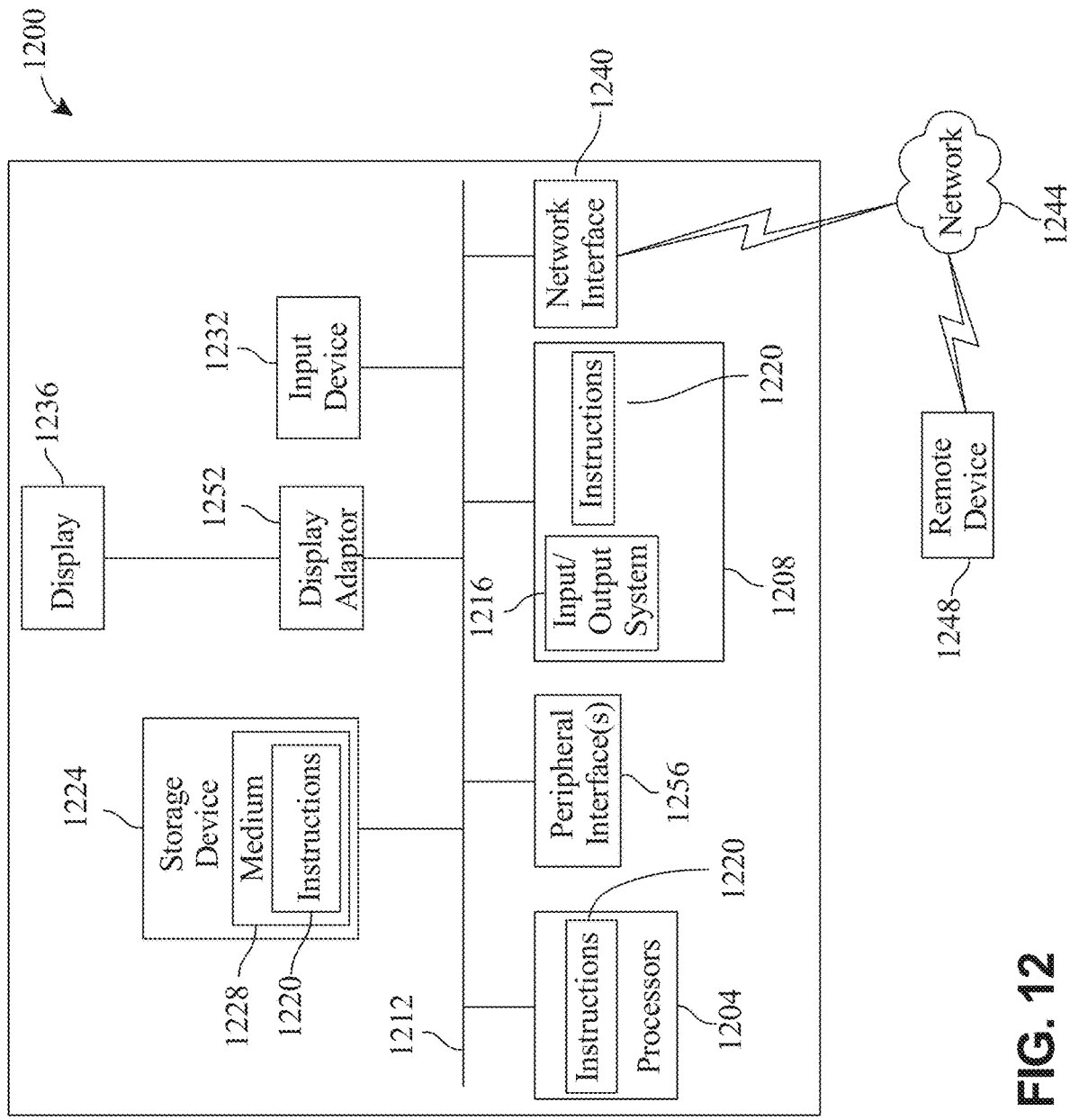
FIG. 12 is a block diagram of a computing system that can be used to implement any one or more of the methodologies disclosed herein and any one or more portions thereof.

FIG. 12 shows a diagrammatic representation of one embodiment of a computing device in the exemplary form of a computer system 1200 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1200 includes a processor 1204 and a memory 1208 that communicate with each other, and with other components, via a bus 1212. Bus 1212 may include any of several types of bus structures including, but not limited to, a memory bus, a memory controller, a peripheral bus, a local bus, and any combinations thereof, using any of a variety of bus architectures.

Processor 1204 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1204 may be organized according to Von Neumann and/or Harvard architecture as a non-limiting example. Processor 1204 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1208 may include various components (e.g., machine-readable media) including, but not limited to, a random-access memory component, a read only component, and any combinations thereof. In one example, a basic input/output system 1216 (BIOS), including basic routines that help to transfer information between elements within computer system 1200, such as during start-up, may be stored in memory 1208. Memory 1208 may also include (e.g., stored on one or more machine-readable media) instructions (e.g., software) 1220 embodying any one or more of the aspects and/or methodologies of the present disclosure. In another example, memory 1208 may further include any number of program modules including, but not limited to, an operating system, one or more application programs, other program modules, program data, and any combinations thereof.

Computer system 1200 may also include a storage device 1224. Examples of a storage device (e.g., storage device 1224) include, but are not limited to, a hard disk drive, a magnetic disk drive, an optical disc drive in combination with an optical medium, a solid-state memory device, and any combinations thereof. Storage device 1224 may be connected to bus 1212 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1224 (or one or more components thereof) may be removably interfaced with computer system 1200 (e.g., via an external port connector (not shown)). Particularly, storage device 1224 and an associated machine-readable medium 1228 may provide nonvolatile and/or volatile storage of machine-readable instructions, data structures, program modules, and/or other data for computer system 1200. In one example, software 1220 may reside, completely or partially, within machine-readable medium 1228. In another example, software 1220 may reside, completely or partially, within processor 1204.

Computer system 1200 may also include an input device 1232. In one example, a user of computer system 1200 may enter commands and/or other information into computer system 1200 via input device 1232. Examples of an input device 1232 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1232 may be interfaced to bus 1212 via any of a variety of interfaces (not shown) including, but not limited to, a serial interface, a parallel interface, a game port, a USB interface, a FIRE-WIRE interface, a direct interface to bus 1212, and any combinations thereof. Input device 1232 may include a touch screen interface that may be a part of or separate from display device 1236, discussed further below. Input device 1232 may be utilized as a user selection device for selecting one or more graphical representations in a graphical interface as described above.

A user may also input commands and/or other information to computer system 1200 via storage device 1224 (e.g., a removable disk drive, a flash drive, etc.) and/or network interface device 1240. A network interface device, such as network interface device 1240, may be utilized for connecting computer system 1200 to one or more of a variety of networks, such as network 1244, and one or more remote devices 1248 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1244, may employ a wired and/or a wireless mode of communication. In general, any network topology may be used. Information (e.g., data, software 1220, etc.) may be communicated to and/or from computer system 1200 via network interface device 1240.

Computer system 1200 may further include a video display adapter 1252 for communicating a displayable image to a display device, such as display device 1236. Examples of a display device include, but are not limited to, a liquid crystal display (LCD), a cathode ray tube (CRT), a plasma display, a light emitting diode (LED) display, and any combinations thereof. Display adapter 1252 and display device 1236 may be utilized in combination with processor 1204 to provide graphical representations of aspects of the present disclosure. In addition to a display device, computer system 1200 may include one or more other peripheral output devices including, but not limited to, an audio speaker, a printer, and any combinations thereof. Such peripheral output devices may be connected to bus 1212 via a peripheral interface 1256. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for training a machine learning model, the apparatus comprising:
at least a processor; and a memory communicatively connected to the at least processor, wherein the memory contains instructions configuring the at least processor to:
receive, from databases via a network, a corpus of data containing entries corresponding to a plurality of subjects;
extract a plurality of entries with identifier within the corpus corresponding to a first subject of the plurality of subjects and represents medical history of the first subject;
execute a temporal attribute machine learning model to determine a plurality of temporal attributes of the plurality of entries from the plurality of entries, wherein at least a temporal attribute of the plurality of temporal attributes is a temporal attribute of an entry of the plurality of entries, wherein the temporal attribute of the plurality of temporal attributes represents time within the medical history, wherein the determining the plurality of temporal attributes comprises:
training, by executing a machine learning process, the temporal attribute machine learning model on a training dataset including the plurality of entries correlated to the plurality of temporal attributes;
generating a temporal attribute as a function of the entry using the trained temporal attribute machine learning model; and
altering the temporal attribute while preserving the temporal attribute's chronological order relative to other temporal attributes of entries having a same subject;
generate automatically, based on the determined plurality of temporal attributes, a plurality of tokens as a function of the plurality of entries, wherein the plurality of tokens comprises tokens of different modalities;
generate a chronological data structure segment comprising the plurality of entries and the plurality of tokens, as a function of the plurality of temporal attributes;
train a multimodal machine learning model on a training dataset including the chronological data structure segment to produce model output including a medical prediction as a medical state of the first subject, wherein the training the multimodal machine learning model comprises computing co-occurrences of the tokens of different modalities to compute degree similarity for the tokens; and
receive, from the trained multimodal machine learning model run on a computing device, the model output.

2. The apparatus of claim 1, wherein: receiving the corpus of data comprises receiving entries from a plurality of medical databases; and the chronological data structure segment comprises an entirety of the first subject's medical history which is recorded in the plurality of medical databases.

3. The apparatus of claim 1, wherein determining the plurality of temporal attributes comprises: training a temporal attribute machine learning model on a training dataset including a plurality of entries correlated to a plurality of temporal attributes; and generating a temporal attribute as a function of a second entry using the trained temporal attribute machine learning model.

4. The apparatus of claim 1, wherein the memory contains instructions configuring the at least processor to deidentify a third entry.

5. The apparatus of claim 4, wherein deidentifying the third entry comprises altering a temporal attribute associated with the third entry while preserving the temporal attribute's chronological order relative to other temporal attributes of entries associated with the same subject.

6. The apparatus of claim 1, wherein: the training dataset comprises a chronological data structure comprising the chronological data structure segment; and the chronological data structure comprises subject medical data of a plurality of subjects divided into a plurality of chronological data structure segments of the chronological data structure.

7. The apparatus of claim 1, wherein: the training dataset comprises a chronological data structure comprising the chronological data structure segment; and the chronological data structure comprises entries of the plurality of entries which are associated with a plurality of subjects.

8. The apparatus of claim 7, wherein each chronological data structure segment of the plurality of chronological data structure segments comprises entries of a single subject.

9. The apparatus of claim 1, wherein the memory contains instructions configuring the at least processor to split the chronological data structure segment at a point between two chronologically adjacent entries.

10. A method of training a machine learning model, the method comprising:
  receiving, from databases via a network, a corpus of data containing entries corresponding to a plurality of subjects;
  extracting, by a processor, a plurality of entries with an identifier within the corpus corresponding to a first subject of the plurality of subjects and representing medical history of the first subject;
  executing a temporal attribute machine learning model to determine a plurality of temporal attributes of the plurality of entries from the plurality of entries, wherein at least a temporal attribute of the plurality of temporal attributes is a temporal attribute of an entry of the plurality of entries, wherein the temporal attribute of the plurality of temporal attributes represents time within the medical history, wherein the determining the plurality of temporal attributes comprises:
    training, by executing a machine learning process, the temporal attribute machine learning model on a training dataset including the plurality of entries correlated to the plurality of temporal attributes;
    generating a temporal attribute as a function of the entry using the trained temporal attribute machine learning model; and
    altering the temporal attribute while preserving the temporal attribute's chronological order relative to other temporal attributes of entries having a same subject;
  generating automatically, based on the determined plurality of temporal attributes, a plurality of tokens as a function of the plurality of entries, wherein the plurality of tokens comprises tokens of a plurality of different modalities;
  generating a chronological data structure segment comprising the plurality of entries and the plurality of tokens, as a function of the plurality of temporal attributes;
  training a multimodal machine learning model on a training dataset including the chronological data structure segment to produce a model output including a medical prediction as a medical state of the first subject, wherein the training the multimodal machine learning model comprises computing co-occurrences of the tokens of different modalities to compute degree similarity for the tokens of different modalities; and
  receiving, from the trained multimodal machine learning model run on a computing device, the model output.

11. The method of claim 10, wherein: receiving the corpus of data comprises receiving entries from a plurality of medical databases; and the chronological data structure segment comprises an entirety of the first subject's medical history which is recorded in the plurality of medical databases.

12. The method of claim 10, wherein determining the plurality of temporal attributes comprises: training a temporal attribute machine learning model on a training dataset including a plurality of entries correlated to a plurality of temporal attributes; and generating a temporal attribute as a function of a second entry using the trained temporal attribute machine learning model.

13. The method of claim 10, wherein method further comprises, using the at least a processor, deidentifying a third entry.

14. The method of claim 13, wherein deidentifying the third entry comprises altering a temporal attribute associated with the third entry while preserving the temporal attribute's chronological order relative to other temporal attributes of entries associated with the same subject.

15. The method of claim 10, wherein: the training dataset comprises a chronological data structure comprising the chronological data structure segment; and the chronological data structure comprises subject medical data of a plurality of subjects divided into a plurality of chronological data structure segments of the chronological data structure.

16. The method of claim 10, wherein: the training dataset comprises a chronological data structure comprising the chronological data structure segment; and the chronological data structure comprises entries of the plurality of entries which are associated with a plurality of subjects.

17. The method of claim 16, wherein each chronological data structure segment of the plurality of chronological data structure segments comprises entries of a single subject.

18. The method of claim 10, wherein the method further comprises, using the at least a processor, splitting the chronological data structure segment at a point between two chronologically adjacent entries.

* * * * *